US007192706B2

(12) United States Patent  
Hafen et al.

(10) Patent No.: US 7,192,706 B2
(45) Date of Patent: Mar. 20, 2007

(54) GROWTH REGULATING PROTEINS

(75) Inventors: Ernst Hafen, Zürich (CH); Hugo Stocker, Zürich (CH); Pierre Daram, Uetikon am See (CH); Benno Shindelholz, Niederlenz (CH); Sebastian Breuer, Singen (DE)

(73) Assignees: Universität Zürich, Schlieren (CH); The Genetics Company, Inc., Zurich (CH)

( * ) Notice: Subject to any disclaimer, the term of this patent is extended or adjusted under 35 U.S.C. 154(b) by 0 days.

(21) Appl. No.: 10/509,558

(22) PCT Filed: Mar. 28, 2003

(86) PCT No.: PCT/IB03/01257

§ 371 (c)(1),
(2), (4) Date: Mar. 25, 2005

(87) PCT Pub. No.: WO03/083113

PCT Pub. Date: Oct. 9, 2003

(65) Prior Publication Data

US 2005/0164194 A1 Jul. 28, 2005

Related U.S. Application Data

(60) Provisional application No. 60/368,457, filed on Mar. 28, 2002.

(51) Int. Cl.
*C12Q 1/68* (2006.01)
*G01N 33/574* (2006.01)
*C07H 21/04* (2006.01)
*C12N 9/64* (2006.01)

(52) U.S. Cl. .................. 435/6; 435/7.23; 435/226; 435/320.1; 435/325; 536/23.2

(58) Field of Classification Search .............. 435/6, 435/7.23, 226, 320.1, 325; 536/23.2
See application file for complete search history.

(56) References Cited

U.S. PATENT DOCUMENTS 5,194,596 A * 3/1993 Tischer et al. ............ 530/399
5,350,836 A * 9/1994 Kopchick et al. ........ 530/399

FOREIGN PATENT DOCUMENTS

WO -WO 02055702 7/2002

OTHER PUBLICATIONS

Haynes et al. Proteome analysis: biological assay or data archive? Electrophoresis 19:1862-1871, 1998.*
Benjamin LE, Hemo I, Keshet E. A plasticity window for blood vessel remodelling is defined by pericyte coverage of the preformed endothelial network and is regulated by PDGF-B and VEGF, Development. May 1998;125(9):1591-8.*
Yukicevic S, Kopp JB, Luyten FP, Sampath TK. Induction of nephrogenic mesenchyme by osteogenic protein 1 (bone morphogenetic protein 7). Proc Natl Acad Sci U S A. Aug. 20, 1996;93(17):9021-6.*
Massague J. The TGF-beta family of growth and differentiation factors. Cell. May 22, 1987;49(4):437-8.*
Pilbeam CC, Alander CB, Simmons HA, Raisz LG. Comparison of the effects of various lengths of synthetic human parathyroid hormone-related peptide (hPTHrP) of malignancy on bone resorption and formation in organ culture. Bone. Sep.-Oct. 1993;14(5):717-20.*
Vogel et al. Dissminated tumor cells—Their detection and significance for prognosis of gastrointestianl and pancreatic carcinomas. Virchows Arch 439:109-117, 2001.*
Skates et al. Molecular markers for early detection of renal carcinoma: investigative approach. Clin Cancer Res. Sep. 15;10(18 Pt 2):6296S-301S, 2004.*
Bunn. Early detection of lung cancer using serum RNA or DNA markers: ready for "prime time" or for validation? J Clin Oncol. Nov. 1;21(21):3891-3, 2003.*
Shaw et al. Future of early detection of lung cancer: the role of mouse models. Clin Cancer Res. Jul. 1; 11(13 Pt 2):4999s-5003s, 2005.*
Nagase, T. et al., "Prediction of the Coding Sequences of Unidentified Human Genes. V. the Coding Sequences of 40 New Genes (KIAA0161-KIAA0200) Deduced by Analysis of CDNA Clones From Human Cell Line KG-1" DNA Research, Univdrsal Academy Press, JP, vol. 3, No. 1, Feb. 29, 1996 pp. 17-24 XP002037754, ISSN: 1340-2838, KIAA0171, Figure 1, Table 1, Table 3.
Database NCBI 'Online!, Oct. 6, 2001 Database Accession No. D79993, SP002245863.
Database EMBL 'Online!, Nov. 15, 2001 Database Accession No. AF434813, XP002245864, Abstract.
Rosenthal, Julie A. et al., "The epsins define a family of prteins that interact with components of the clathrin coat and contain a new protein module." Journal of Biological Chemistry, vol. 274, No. 48, Nov. 26, 1999, pp. 33959-33965, XP002245872, ISSN: 0021-9258, Figures 1, 2.
Xu, T. et al., "Identifying tumor suppressors in genetic mosaics: the *Drosophila lats* gene encodes a putative protein kinase" Development, Company of Biologists, Cambridge, GB, vol. 121, No. 4, 1995, pp. 1053-1063, XP002103731, ISSN: 0950-1991, p. 1054, Right-hand Column, Paragraph 2, p. 1055, Right-Hand Column, Paragraph 3, Figure 2.
Tao, W. et al., "Human homologue of the *Drosophila melanogaster lats* tumour suppressor modulates CDC2 activity" Nature Genetics, New York, NY, US, vol. 21, Feb. 1999, pp. 177-181, XP002103732, ISSN: 1061-4036, p. 178, Left-hand Column, Paragraph 1, p. 179, Left-hand Column, Paragraph 1.

(Continued)

*Primary Examiner*—Janet L. Andres
*Assistant Examiner*—Gregory S Emch
(74) *Attorney, Agent, or Firm*—Marshall, Gerstein & Borun LLP

(57) ABSTRACT

The application discloses a new family of proteins, namely the epsin like proteins (ELP). Said proteins comprise an ENTH domain (Epsin NH2 Terminal Homology domain) and have growth inhibiting activity. The disclosed proteins can be used for the diagnosis of hyperproliferative diseases as well as for gene therapy purposes.

7 Claims, 6 Drawing Sheets

OTHER PUBLICATIONS

St. John M.A.R. et al., "Mice Deficient of LATS1 Develop Soft-Tissue Sarcomas, Ovarian Tumours and Pituitary Dysfunction" Nature Genetics, Nature America, New York, US, vol. 21, Feb. 1999, pp. 182-186, XP002923457, ISSN: 1061-4036, Abstract, p. 184, Left-hand Column, Paragraph 2, Right-hand Column, Paragraph,1, p. 185, Left-hand Column, Paragraph 2, Right-hand Column, Paragraph 1.

Eichmuller et al., "The human EMAP-like protein 70 (ELP70) is a microtubule destabilizer that locates to the mitotic apparatus," Journal of Biolgical Chemistry, vol. 277, No. 2, Jan. 11, 2002, pp. 1301-1309.

International Search Report corresponding to International Patent Application Serial No. PCT/IB03/01257, dated Sep. 22, 2003, 7 pages.

* cited by examiner wild type        ELP mutant

Fig. 2

( ⇩ Drosophila mutants)

```
                                          ⇩
d-epsin   1  MVDKFSMWKVRELADKVTNVVMNYETEGKVREATNDDPWGPHGPLMQEIAYSTFSVET
h-epsin   1  ....MENMWKVRELVDKATNVVMNYEIESKVREATNDDPWGPSGQLMGEIAKATBMYEQ d-epsin  61  FPEMSMLWKRMLQDNKTNWRRTYKSLLLLNYLHRNGSERVVTSSREHIYDLRSLENYTF
h-epsin  57  FPEMNMLWSRMLKDNKKNWRRVYKSLLLLAYLHRNGSERVVTSAREHIYDLRSLENYHF d-epsin 121  TDEGGKDQGINVRHKVRELHTFIQDDDRLREERKKAKKNKDKYHGNSSDAMGMRSGGKSG
h-epsin 117  VDEHGKDQGINTRQKVFELVEFAQDDDRLREERKKAKKNKDKYVGVSSDSN....GGER.

d-epsin 181  YSGGSGGGGGGSGGYNDGPIRSSKGDNWVSDK...SADKDRYEDDDTHYDGEREGSDSDS
h-epsin 172  YSER.YDPEPKSKW..DEEDDKNKSAFPESDKLGELSDKIGSTIDDTISKFRRKDRS.DS
                                          ⇩
d-epsin 238  PSPRRNYRYNKRASPAEVASEAKPSSLNMNIRSKTVSSPVSKQPTSTASAKPALSQKKID
h-epsin 227  PE..RCSDSDEESKARRGRSPKGEFKDEEETVTKHHHITQATETTHTRHKRTANPSKTID d-epsin 298  LGAAANE..GKPAPGGAAGIHSPTHRDTPTSVDLMGGASPSPSTSKNNHKQSNNNDILD
h-epsin 287  LGAAAHFTGDKASPDQNASTHGP.QSSVKTSVPSSKSSGDLVDLFDETSDSTGGSADLFG d-epsin 354  DL..FKICSPPPG..QEKTLNSTAVIVDDDDDFNPRASDISQQEFGDFASAFGQPSAGST
h-epsin 346  GFADEGEAAASGSFPSQVIATSGNGDFGDWSAFN.QAPSCPVASSCFFGSASDPAVELV d-epsin 413  ISEPPSTCLVPAA...NDEFADFFAFQSTTSESAIDGNFKTATPANDSFDFFNSAPTS
h-epsin 405  SGSQSALCPPPAASNSSDLFDLMCSSQMMTSQSFNFSMMSTNT.VGLGLPFSRSQNID d-epsin 469  TAAAYTATDLLAGLGDLSFHQSMP...WDNMMPPIPAVTG.NNFKQPMSVTNNN..NTNG
h-epsin 464  MVQKFVSKTLPSTWSDPSFNISFDNLFPGMQPSKPQQPSLNTMQQQNMQFPMNVMTQSF d-epsin 524  GAVPAAASVFSTAVGATWFGDLKGGKMNFDDDNFFMSKSG.KPSFPAPSMNALKTNSPAK
h-epsin 524  GAVNLSSPSFMLPV.RPQFNALIGGPMPFSLPNFFTGTMGMAPLFNTPMVNQSMMGMNMN d-epsin 583  APFNVQTGGGFPCLSPMTSPNIIFGAPAPQQFPQNQSAFANFFAFQQQQQNHSNNNNNSS
h-epsin 583  IGMSA.AGMGLTGTMGMGMPNI...AMTSGFQPKQDAFANFFNFSK............

d-epsin 643  SAFDLFQ
h-epsin 626  .......
```

Fig. 3

```
h-18aaELP    MLNMWKVRELVDKATNVVMNYSEIESKVREATNDDPWGPSGQLMGEIAKATFMYEQFPEL 60
h-ELP        MLNMWKVRELVDKATNVVMNYSEIESKVREATNDDPWGPSGQLMGEIAKATFMYEQFPEL 60
             ************************************************************ h-18aaELP    MNMLWSRMLKDNKKNWRRVYKSLLLLAYLIRNGSERVVTSAREHIYDLRSLENYHFVDEH 120
h-ELP        MNMLWSRMLKDNKKNWRRVYKSLLLLAYLIRNGSERVVTSAREHIYDLRSLENYHFVDEH 120
             ************************************************************ h-18aaELP    GKDQGINIRQKVKELVEFAQDDDRLREERKKAKKNKDKYVGVSSDSVGGFRYSERYDPEP 180
h-ELP        GKDQGINIRQKVKELVEFAQDDDRLREERKKAKKNKDKYVGVSSDSVGGFRYSERYDPEP 180
             ************************************************************ h-18aaELP    KSKWDEEWDKNKSAFPFSDKLGELSDKIGSTIDDTISKFRRKDREDSPERCSDSDEEKKA 240
h-ELP        KSKWDEEWDKNKSAFPFSDKLGELSDKIGSTIDDTISKFRRKDREDSPERCSDSDEEKKA 240
             ************************************************************ h-18aaELP    RRGRSPKGEFKDEEETVTTKHIHITQATETTTTRHKRTANPSKTIDLGAAAHYTGDKASP 300
h-ELP        RRGRSPKGEFKDEEETVTTKHIHITQATETTTTRHKRTANPSKTIDLGAAAHYTGDKASP 300
             ************************************************************ h-18aaELP    DQNASTHTPQSSVKTSVPSSKSSGDLVDLFDGTSQSTGGSADLFGGFADFGSAAASGSFP 360
h-ELP        DQNASTHTPQSSVKTSVPSSKSSGDLVDLFDGTSQSTGGSADLFGGFADFGSAAASGSFP 360
             ************************************************************ h-18aaELP    SQVTATSGNGDFGDWSAFNQAPSGPVASSGEFFGSASQPAVELVSGSQSALGPPPAASNS 420
h-ELP        SQVTATSGNGDFGDWSAFNQAPSGPVASSGEFFGSASQPAVELVSGSQSALGPPPAASNS 420
             ************************************************************ h-18aaELP    SDLFDLMGSSQATMTSSQSMNFSMMSTNTVGLGLPMSRSQPLQNVSTVLQKPNPLYNQNT 480
h-ELP        SDLFDLMGSSQATMTSSQSMNFSMMSTNTVGLGLPMSRSQ------------------NT 462
             ************************************** h-18aaELP    DMVQKSVSKTLPSTWSDPSVNISLDNLLPGMQPSKPQQPSLNTMIQQQNMQQPMNVMTQS 540
h-ELP        DMVQKSVSKTLPSTWSDPSVNISLDNLLPGMQPSKPQQPSLNTMIQQQNMQQPMNVMTQS 522
             ************************************************************ h-18aaELP    FGAVNLSSPSNMLPVRPQTNALIGGPMPMSMPNVMTGTMGMAPLGNTPMMNQSMMGMNMN 600
h-ELP        FGAVNLSSPSNMLPVRPQTNALIGGPMPMSMPNVMTGTMGMAPLGNTPMMNQSMMGMNMN 582
             ************************************************************ h-18aaELP    IGMSAAGMGLTGTMGMGMPNIAMTSGTVQPKQDAFANFANFSK 643
h-ELP        IGMSAAGMGLTGTMGMGMPNIAMTSGTVQPKQDAFANFANFSK 625
             ******************************************
```

Fig. 6
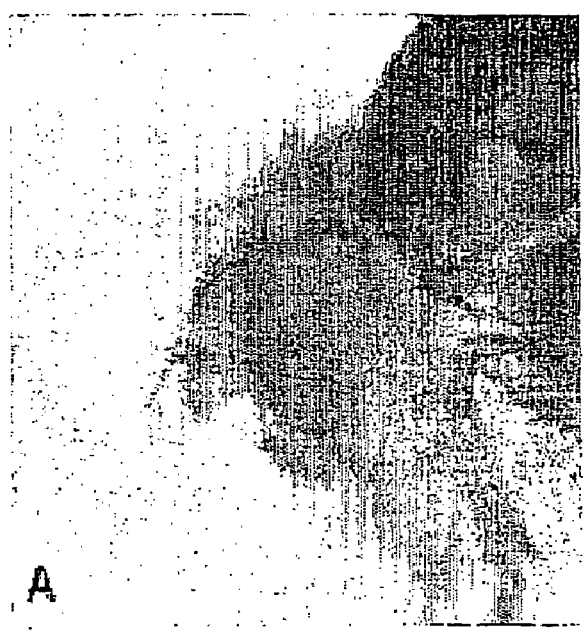

SEQUENCE LISTING

```
<160> NUMBER OF SEQ ID NOS: 5

<210> SEQ ID NO 1
<211> LENGTH: 2096
<212> TYPE: DNA
<213> ORGANISM: Homo sapiens
<220> FEATURE:
<221> NAME/KEY: CDS
<222> LOCATION: (76)..(1950)
<223> OTHER INFORMATION:

<400> SEQUENCE: 1
ggcacgaggc ggaagtgttc cggggtccgt ggggagcagg agagggaggc ggcggaccgt      60
cccgcgcggg gcacg atg ttg aac atg tgg aag gtg cgc gag ctg gtg gac     111
              Met Leu Asn Met Trp Lys Val Arg Glu Leu Val Asp
                1               5                  10 aaa gcc acc aat gtt gtt atg aat tat tca gag atc gag tct aag gtt     159
Lys Ala Thr Asn Val Val Met Asn Tyr Ser Glu Ile Glu Ser Lys Val
          15                  20                  25 cga gag gca acg aac gat gat cct tgg gga cct tct ggg caa ctc atg     207
Arg Glu Ala Thr Asn Asp Asp Pro Trp Gly Pro Ser Gly Gln Leu Met
     30                  35                  40 gga gag att gcc aag gct aca ttt atg tat gaa caa ttt cca gaa ctt     255
Gly Glu Ile Ala Lys Ala Thr Phe Met Tyr Glu Gln Phe Pro Glu Leu
45                  50                  55                  60
```

```
atg aac atg ctt tgg tca cga atg tta aaa gac aac aaa aag aat tgg      303
Met Asn Met Leu Trp Ser Arg Met Leu Lys Asp Asn Lys Lys Asn Trp
             65                  70                  75 aga aga gtt tat aag tcg ttg ctg ctc cta gct tac ctc ata agg aat      351
Arg Arg Val Tyr Lys Ser Leu Leu Leu Leu Ala Tyr Leu Ile Arg Asn
         80                  85                  90 gga tca gag cgt gtt gtt aca agt gcc aga gaa cac att tat gat tta      399
Gly Ser Glu Arg Val Val Thr Ser Ala Arg Glu His Ile Tyr Asp Leu
     95                 100                 105 cga tcc ctg gaa aat tac cac ttt gta gat gag cat ggt aag gat caa      447
Arg Ser Leu Glu Asn Tyr His Phe Val Asp Glu His Gly Lys Asp Gln
 110                 115                 120 ggt ata aat att cga cag aag gtg aag gaa ttg gtt gaa ttt gcc cag      495
Gly Ile Asn Ile Arg Gln Lys Val Lys Glu Leu Val Glu Phe Ala Gln
125                 130                 135                 140 gat gac gac agg ctt cgt gaa gag cga aag aaa gca aag aag aac aaa      543
Asp Asp Asp Arg Leu Arg Glu Glu Arg Lys Lys Ala Lys Lys Asn Lys
                 145                 150                 155 gac aag tat gtt ggg gtt tcc tca gac agt gtt gga gga ttc aga tac      591
Asp Lys Tyr Val Gly Val Ser Ser Asp Ser Val Gly Gly Phe Arg Tyr
             160                 165                 170 agt gaa aga tat gat cct gag ccc aaa tca aaa tgg gat gag gag tgg      639
Ser Glu Arg Tyr Asp Pro Glu Pro Lys Ser Lys Trp Asp Glu Glu Trp
         175                 180                 185 gat aaa aac aag agt gct ttt cca ttc agt gat aaa tta ggt gag ctg      687
Asp Lys Asn Lys Ser Ala Phe Pro Phe Ser Asp Lys Leu Gly Glu Leu
     190                 195                 200 agt gat aaa att gga agc aca att gat gac acc atc agc aag ttc cgg      735
Ser Asp Lys Ile Gly Ser Thr Ile Asp Asp Thr Ile Ser Lys Phe Arg
205                 210                 215                 220 agg aaa gat aga gaa gac tct cca gaa aga tgc agc gac agc gat gag      783
Arg Lys Asp Arg Glu Asp Ser Pro Glu Arg Cys Ser Asp Ser Asp Glu
                 225                 230                 235 gaa aag aaa gcg aga aga ggc aga tct ccc aaa ggt gaa ttc aaa gat      831
Glu Lys Lys Ala Arg Arg Gly Arg Ser Pro Lys Gly Glu Phe Lys Asp
             240                 245                 250 gaa gag gag act gtg acg aca aag cat att cat atc aca cag gcc aca      879
Glu Glu Glu Thr Val Thr Thr Lys His Ile His Ile Thr Gln Ala Thr
         255                 260                 265 gag acc acc aca acc aga cac aag cgc aca gca aat cct tcc aaa acc      927
Glu Thr Thr Thr Thr Arg His Lys Arg Thr Ala Asn Pro Ser Lys Thr
     270                 275                 280 att gat ctt gga gca gca gca cat tac aca ggg gac aaa gca agt cca      975
Ile Asp Leu Gly Ala Ala Ala His Tyr Thr Gly Asp Lys Ala Ser Pro
285                 290                 295                 300 gat cag aat gct tca acc cac aca cct cag tct tca gtt aag act tca     1023
Asp Gln Asn Ala Ser Thr His Thr Pro Gln Ser Ser Val Lys Thr Ser
                 305                 310                 315 gtg cct agc agc aag tca tct ggt gac ctt gtt gat ctg ttt gat ggc     1071
Val Pro Ser Ser Lys Ser Ser Gly Asp Leu Val Asp Leu Phe Asp Gly
             320                 325                 330 acc agc cag tca aca gga gga tca gct gat tta ttc gga gga ttt gct     1119
Thr Ser Gln Ser Thr Gly Gly Ser Ala Asp Leu Phe Gly Gly Phe Ala
         335                 340                 345 gac ttt ggc tca gct gct gca tca ggc agt ttc cct tcc caa gta aca     1167
Asp Phe Gly Ser Ala Ala Ala Ser Gly Ser Phe Pro Ser Gln Val Thr
     350                 355                 360 gca aca agt ggg aat gga gac ttt ggt gac tgg agt gcc ttc aac caa     1215
Ala Thr Ser Gly Asn Gly Asp Phe Gly Asp Trp Ser Ala Phe Asn Gln
365                 370                 375                 380
```

```
gcc cca tca ggc cct gtt gct tcc agt ggc gag ttc ttt ggc agt gcc    1263
Ala Pro Ser Gly Pro Val Ala Ser Ser Gly Glu Phe Phe Gly Ser Ala
            385                 390                 395 tca cag cca gcg gta gaa ctt gtt agt ggc tca caa tca gct cta ggc    1311
Ser Gln Pro Ala Val Glu Leu Val Ser Gly Ser Gln Ser Ala Leu Gly
        400                 405                 410 cca cct cct gct gcc tca aat tct tca gac ctg ttt gat ctt atg ggc    1359
Pro Pro Pro Ala Ala Ser Asn Ser Ser Asp Leu Phe Asp Leu Met Gly
    415                 420                 425 tcg tcc cag gca acc atg aca tct tcc cag agt atg aat ttc tct atg    1407
Ser Ser Gln Ala Thr Met Thr Ser Ser Gln Ser Met Asn Phe Ser Met
430                 435                 440 atg agc act aac act gtg gga ctt ggt ttg cct atg tca aga tca cag    1455
Met Ser Thr Asn Thr Val Gly Leu Gly Leu Pro Met Ser Arg Ser Gln
445                 450                 455                 460 aat aca gat atg gtc cag aaa tca gtc agc aaa acc ttg ccc tct act    1503
Asn Thr Asp Met Val Gln Lys Ser Val Ser Lys Thr Leu Pro Ser Thr
                465                 470                 475 tgg tct gac ccc agt gta aac atc agc cta gac aac tta cta cct ggt    1551
Trp Ser Asp Pro Ser Val Asn Ile Ser Leu Asp Asn Leu Leu Pro Gly
            480                 485                 490 atg cag cct tcc aaa ccc cag cag cca tca ctg aat aca atg att cag    1599
Met Gln Pro Ser Lys Pro Gln Gln Pro Ser Leu Asn Thr Met Ile Gln
        495                 500                 505 caa cag aat atg cag cag cct atg aat gtg atg act caa agt ttt gga    1647
Gln Gln Asn Met Gln Gln Pro Met Asn Val Met Thr Gln Ser Phe Gly
    510                 515                 520 gct gtg aac ctc agt tct cca tcg aac atg ctt cct gtc cgg ccc caa    1695
Ala Val Asn Leu Ser Ser Pro Ser Asn Met Leu Pro Val Arg Pro Gln
525                 530                 535                 540 act aat gct ttg ata ggg gga ccc atg cct atg agc atg ccc aat gtg    1743
Thr Asn Ala Leu Ile Gly Gly Pro Met Pro Met Ser Met Pro Asn Val
                545                 550                 555 atg act ggc acc atg gga atg gcc cct ctt gga aat act ccg atg atg    1791
Met Thr Gly Thr Met Gly Met Ala Pro Leu Gly Asn Thr Pro Met Met
            560                 565                 570 aac cag agc atg atg ggc atg aac atg aac ata ggg atg tcc gct gct    1839
Asn Gln Ser Met Met Gly Met Asn Met Asn Ile Gly Met Ser Ala Ala
        575                 580                 585 ggg atg ggc ttg aca ggc aca atg gga atg ggc atg ccc aac ata gcc    1887
Gly Met Gly Leu Thr Gly Thr Met Gly Met Gly Met Pro Asn Ile Ala
    590                 595                 600 atg act tct gga act gtg caa ccc aag caa gat gcc ttt gca aat ttc    1935
Met Thr Ser Gly Thr Val Gln Pro Lys Gln Asp Ala Phe Ala Asn Phe
605                 610                 615                 620 gcc aat ttt agc aaa taagagattg taaagaagc agattgaatg aagaattttt    1990
Ala Asn Phe Ser Lys
                625 agctgtgcag ataggtgatg ttgggatgga aaatgctaat caactaccct ttctttatc   2050 aagtaattaa aataaatcta cataaaaaaa aaaaaaaaa aaaaaa                  2096

<210> SEQ ID NO 2
<211> LENGTH: 625
<212> TYPE: PRT
<213> ORGANISM: Homo sapiens

<400> SEQUENCE: 2

Met Leu Asn Met Trp Lys Val Arg Glu Leu Val Asp Lys Ala Thr Asn
1               5                   10                  15
```

-continued

```
Val Val Met Asn Tyr Ser Glu Ile Glu Ser Lys Val Arg Glu Ala Thr
            20                  25                  30

Asn Asp Asp Pro Trp Gly Pro Ser Gly Gln Leu Met Gly Glu Ile Ala
        35                  40                  45

Lys Ala Thr Phe Met Tyr Glu Gln Phe Pro Glu Leu Met Asn Met Leu
    50                  55                  60

Trp Ser Arg Met Leu Lys Asp Asn Lys Asn Trp Arg Arg Val Tyr
65                  70                  75                  80

Lys Ser Leu Leu Leu Leu Ala Tyr Leu Ile Arg Asn Gly Ser Glu Arg
                85                  90                  95

Val Val Thr Ser Ala Arg Glu His Ile Tyr Asp Leu Arg Ser Leu Glu
            100                 105                 110

Asn Tyr His Phe Val Asp Glu His Gly Lys Asp Gln Gly Ile Asn Ile
            115                 120                 125

Arg Gln Lys Val Lys Glu Leu Val Glu Phe Ala Gln Asp Asp Asp Arg
130                 135                 140

Leu Arg Glu Glu Arg Lys Lys Ala Lys Lys Asn Lys Asp Lys Tyr Val
145                 150                 155                 160

Gly Val Ser Ser Asp Ser Val Gly Gly Phe Arg Tyr Ser Glu Arg Tyr
                165                 170                 175

Asp Pro Glu Pro Lys Ser Lys Trp Asp Glu Trp Asp Lys Asn Lys
            180                 185                 190

Ser Ala Phe Pro Phe Ser Asp Lys Leu Gly Glu Leu Ser Asp Lys Ile
            195                 200                 205

Gly Ser Thr Ile Asp Asp Thr Ile Ser Lys Phe Arg Arg Lys Asp Arg
            210                 215                 220

Glu Asp Ser Pro Glu Arg Cys Ser Asp Ser Asp Glu Lys Lys Ala
225                 230                 235                 240

Arg Arg Gly Arg Ser Pro Lys Gly Glu Phe Lys Asp Glu Glu Thr
                245                 250                 255

Val Thr Thr Lys His Ile His Ile Thr Gln Ala Thr Glu Thr Thr Thr
            260                 265                 270

Thr Arg His Lys Arg Thr Ala Asn Pro Ser Lys Thr Ile Asp Leu Gly
        275                 280                 285

Ala Ala Ala His Tyr Thr Gly Asp Lys Ala Ser Pro Asp Gln Asn Ala
    290                 295                 300

Ser Thr His Thr Pro Gln Ser Ser Val Lys Thr Ser Val Pro Ser Ser
305                 310                 315                 320

Lys Ser Ser Gly Asp Leu Val Asp Leu Phe Asp Gly Thr Ser Gln Ser
                325                 330                 335

Thr Gly Gly Ser Ala Asp Leu Phe Gly Phe Ala Asp Phe Gly Ser
            340                 345                 350

Ala Ala Ala Ser Gly Ser Phe Pro Ser Gln Val Thr Ala Thr Ser Gly
            355                 360                 365

Asn Gly Asp Phe Gly Asp Trp Ser Ala Phe Asn Gln Ala Pro Ser Gly
    370                 375                 380

Pro Val Ala Ser Ser Gly Glu Phe Phe Gly Ser Ala Ser Gln Pro Ala
385                 390                 395                 400

Val Glu Leu Val Ser Gly Ser Gln Ser Ala Leu Gly Pro Pro Ala
                405                 410                 415

Ala Ser Asn Ser Ser Asp Leu Phe Asp Leu Met Gly Ser Ser Gln Ala
            420                 425                 430
```

-continued

```
Thr Met Thr Ser Ser Gln Ser Met Asn Phe Ser Met Met Ser Thr Asn
        435                 440                 445

Thr Val Gly Leu Gly Leu Pro Met Ser Arg Ser Gln Asn Thr Asp Met
        450                 455                 460

Val Gln Lys Ser Val Ser Lys Thr Leu Pro Ser Thr Trp Ser Asp Pro
465                 470                 475                 480

Ser Val Asn Ile Ser Leu Asp Asn Leu Leu Pro Gly Met Gln Pro Ser
                485                 490                 495

Lys Pro Gln Gln Pro Ser Leu Asn Thr Met Ile Gln Gln Asn Met
        500                 505                 510

Gln Gln Pro Met Asn Val Met Thr Gln Ser Phe Gly Ala Val Asn Leu
        515                 520                 525

Ser Ser Pro Ser Asn Met Leu Pro Val Arg Pro Gln Thr Asn Ala Leu
    530                 535                 540

Ile Gly Gly Pro Met Pro Met Ser Met Pro Asn Val Met Thr Gly Thr
545                 550                 555                 560

Met Gly Met Ala Pro Leu Gly Asn Thr Pro Met Met Asn Gln Ser Met
                565                 570                 575

Met Gly Met Asn Met Asn Ile Gly Met Ser Ala Ala Gly Met Gly Leu
                580                 585                 590

Thr Gly Thr Met Gly Met Gly Met Pro Asn Ile Ala Met Thr Ser Gly
        595                 600                 605

Thr Val Gln Pro Lys Gln Asp Ala Phe Ala Asn Phe Ala Asn Phe Ser
        610                 615                 620

Lys
625

<210> SEQ ID NO 3
<211> LENGTH: 2705
<212> TYPE: DNA
<213> ORGANISM: Drosophila melanogaster
<220> FEATURE:
<221> NAME/KEY: CDS
<222> LOCATION: (262)..(2208)
<223> OTHER INFORMATION:

<400> SEQUENCE: 3
ggacacgaca gctcaccaaa tattagctgc tgtgattttg ttttacaatt ttcgtttaaa      60
tttttacatt tttgtttgcg gaaagcgcgg gtgcgagaca ggtgcgccgt ttccatgcaa     120
aagtgcaaat cgtcagctgc aaaacagtca gaaaacggca cgccaagcga aaacgagttc     180
gacgtcttgt tgtagttgga ttttccagcc acttttcgac gagattgtgt gaaaaattcc     240
gtagcattca atagtctcaa a atg gtg gat aaa ttc atc agc atg tgg aaa       291
                         Met Val Asp Lys Phe Ile Ser Met Trp Lys
                         1               5                   10 gtg cgc gaa ttg gcg gac aag gtc acc aat gtc gtg atg aat tac acg      339
Val Arg Glu Leu Ala Asp Lys Val Thr Asn Val Val Met Asn Tyr Thr
            15                  20                  25 gaa acg gag ggc aag gtg cgg gag gcc acc aac gat gat cct tgg ggg      387
Glu Thr Glu Gly Lys Val Arg Glu Ala Thr Asn Asp Asp Pro Trp Gly
        30                  35                  40 cct aca gga ccc ctc atg cag gaa ttg gcc tat tcc acc ttc tca tac      435
Pro Thr Gly Pro Leu Met Gln Glu Leu Ala Tyr Ser Thr Phe Ser Tyr
    45                  50                  55 gaa aca ttc ccg gag gtg atg tcc atg ctg tgg aag cgc atg ctg cag      483
Glu Thr Phe Pro Glu Val Met Ser Met Leu Trp Lys Arg Met Leu Gln
60                  65                  70
```

-continued

| | | |
|---|---|---|
| gac aat aaa acc aac tgg cga cgc acg tac aag agc ctc ctt ctg cta<br>Asp Asn Lys Thr Asn Trp Arg Arg Thr Tyr Lys Ser Leu Leu Leu Leu<br>75                      80                        85                        90 | 531 |
| aac tat ttg gtg cga aac ggc tct gaa cgg gtg gta acc tcc tct cgg<br>Asn Tyr Leu Val Arg Asn Gly Ser Glu Arg Val Val Thr Ser Ser Arg<br>                      95                        100                      105 | 579 |
| gag cac atc tac gat ctg cgc tcg ctg gag aac tat aca ttc acc gac<br>Glu His Ile Tyr Asp Leu Arg Ser Leu Glu Asn Tyr Thr Phe Thr Asp<br>                110                       115                     120 | 627 |
| gag ggc ggc aag gat cag ggt att aat gtt agg cat aag gta cga gag<br>Glu Gly Gly Lys Asp Gln Gly Ile Asn Val Arg His Lys Val Arg Glu<br>        125                     130                     135 | 675 |
| ctt ata gac ttt att cag gat gat gat cgt ttg cgc gag gag cgc aaa<br>Leu Ile Asp Phe Ile Gln Asp Asp Asp Arg Leu Arg Glu Glu Arg Lys<br>140                       145                     150 | 723 |
| aag gcg aag aag aac aag gac aag tac atc ggc atg agc agc gac gcc<br>Lys Ala Lys Lys Asn Lys Asp Lys Tyr Ile Gly Met Ser Ser Asp Ala<br>155                       160                     165              170 | 771 |
| atg ggc atg cga agc ggt ggc tac agc ggc tat agc ggt gga tct gga<br>Met Gly Met Arg Ser Gly Gly Tyr Ser Gly Tyr Ser Gly Gly Ser Gly<br>                175                     180                     185 | 819 |
| gga ggc ggc ggt ggc agc ggt ggc tac aat gat ggc gac tat cgc tct<br>Gly Gly Gly Gly Gly Ser Gly Gly Tyr Asn Asp Gly Asp Tyr Arg Ser<br>        190                     195                     200 | 867 |
| agt cgt gga gac aat tgg tac tcc gac aaa agc gcc gac aag gat cgg<br>Ser Arg Gly Asp Asn Trp Tyr Ser Asp Lys Ser Ala Asp Lys Asp Arg<br>                205                     210                   215 | 915 |
| tat gag gat gat gat act cac tac gat gga gag cga gag gga tcc gat<br>Tyr Glu Asp Asp Asp Thr His Tyr Asp Gly Glu Arg Glu Gly Ser Asp<br>        220                     225                     230 | 963 |
| agc gac tca ccc agt cca aga cgt aac tat cga tac aat gac cgt gcg<br>Ser Asp Ser Pro Ser Pro Arg Arg Asn Tyr Arg Tyr Asn Asp Arg Ala<br>235                       240                     245              250 | 1011 |
| agt cct gcc gaa gta gcc agc gag gcc aaa cct tcc agc ctc aac atg<br>Ser Pro Ala Glu Val Ala Ser Glu Ala Lys Pro Ser Ser Leu Asn Met<br>                      255                     260                     265 | 1059 |
| aac att cgt tcg aag acc gtc agt tcc cct gtc tcc aag cag ccc act<br>Asn Ile Arg Ser Lys Thr Val Ser Ser Pro Val Ser Lys Gln Pro Thr<br>        270                     275                     280 | 1107 |
| tca acg gct tct gcc aag cca gcg ctg tcc cag aag aag atc gat ctg<br>Ser Thr Ala Ser Ala Lys Pro Ala Leu Ser Gln Lys Lys Ile Asp Leu<br>        285                     290                     295 | 1155 |
| ggt gcg gca gca aac ttt gga aag cca gct cct ggc ggt gct gct ggc<br>Gly Ala Ala Ala Asn Phe Gly Lys Pro Ala Pro Gly Gly Ala Ala Gly<br>300                       305                     310 | 1203 |
| att cac tca cca act cac cgt gac act ccc acc agc gtg gac ttg atg<br>Ile His Ser Pro Thr His Arg Asp Thr Pro Thr Ser Val Asp Leu Met<br>315                       320                     325              330 | 1251 |
| ggc ggc gct tcg cca tcg ccg tct act tcc aag gca aac aat aat acg<br>Gly Gly Ala Ser Pro Ser Pro Ser Thr Ser Lys Ala Asn Asn Asn Thr<br>                335                     340                     345 | 1299 |
| caa agc aat aac aac gat ctg ctg gac gat ctg ttc aag acc tgc tcg<br>Gln Ser Asn Asn Asn Asp Leu Leu Asp Asp Leu Phe Lys Thr Cys Ser<br>        350                     355                     360 | 1347 |
| cca ccg ccg ggg cag gag aag acg ctg aac agt gct gcc gtg att gtg<br>Pro Pro Pro Gly Gln Glu Lys Thr Leu Asn Ser Ala Ala Val Ile Val<br>        365                     370                     375 | 1395 |
| gat gac gat gat gac ttc aat ccg cgt gcc agc gat gct agc cag cag<br>Asp Asp Asp Asp Asp Phe Asn Pro Arg Ala Ser Asp Ala Ser Gln Gln<br>380                       385                     390 | 1443 |

```
gaa ttc ggc gac ttc gcc tct gct ttc ggg cag ccc tcg gcg gga tcg    1491
Glu Phe Gly Asp Phe Ala Ser Ala Phe Gly Gln Pro Ser Ala Gly Ser
395                 400                 405                 410 acg atc agc gag cca cca tca acg ggc ctg gtt ccg gct gcg aac gat    1539
Thr Ile Ser Glu Pro Pro Ser Thr Gly Leu Val Pro Ala Ala Asn Asp
                415                 420                 425 gag ttc gcc gac ttt gcg gcg ttc caa ggc tcg aca acg tcg aca tct    1587
Glu Phe Ala Asp Phe Ala Ala Phe Gln Gly Ser Thr Thr Ser Thr Ser
            430                 435                 440 gcg ctg gac ggt aat ttg ctg aag act gcc acg ccg gcg aac gat tcg    1635
Ala Leu Asp Gly Asn Leu Leu Lys Thr Ala Thr Pro Ala Asn Asp Ser
        445                 450                 455 ttt gac ctg ttt aat tca gct ccc acc tcg acg gca gca gcc aca acg    1683
Phe Asp Leu Phe Asn Ser Ala Pro Thr Ser Thr Ala Ala Ala Thr Thr
460                 465                 470 gct aca gat ctc ctg gca ggc ctg ggc gat ctg tcc att cac caa agc    1731
Ala Thr Asp Leu Leu Ala Gly Leu Gly Asp Leu Ser Ile His Gln Ser
475                 480                 485                 490 atg ccc atg gac aat atg atg cct ccc att ccc gcc gtc acg ggc aat    1779
Met Pro Met Asp Asn Met Met Pro Pro Ile Pro Ala Val Thr Gly Asn
                495                 500                 505 aat ctg ctc cag ccc atg tcg gtg acc aat aat aac aat aat acc aac    1827
Asn Leu Leu Gln Pro Met Ser Val Thr Asn Asn Asn Asn Asn Thr Asn
            510                 515                 520 gga ggc gca gtc ccc gcc gct gcc agt gtc cag tct acc gct gtg ggc    1875
Gly Gly Ala Val Pro Ala Ala Ala Ser Val Gln Ser Thr Ala Val Gly
        525                 530                 535 gcc acc tgg tcg ggc gac ctg aag ggc ggc aag atg aac att gac ctg    1923
Ala Thr Trp Ser Gly Asp Leu Lys Gly Gly Lys Met Asn Ile Asp Leu
540                 545                 550 gac aat ctg ctg atg agc aag tcg ggc aag ccc agt gcc ccg gcc cct    1971
Asp Asn Leu Leu Met Ser Lys Ser Gly Lys Pro Ser Ala Pro Ala Pro
555                 560                 565                 570 tcg atg aat gcc ctg aag acc aac agt ccg gca aag gcg cca ctg aat    2019
Ser Met Asn Ala Leu Lys Thr Asn Ser Pro Ala Lys Ala Pro Leu Asn
                575                 580                 585 gtg cag acg ggt ggc gga ttc cct gga ctg tcg cca atg acc agt ccg    2067
Val Gln Thr Gly Gly Gly Phe Pro Gly Leu Ser Pro Met Thr Ser Pro
            590                 595                 600 aac att ttt ggg gct ccg gca ccg cag caa agc att cca caa aac caa    2115
Asn Ile Phe Gly Ala Pro Ala Pro Gln Gln Ser Ile Pro Gln Asn Gln
        605                 610                 615 tca gca ttt gcc aac ttt gga gct ttc cag cag cag cag cag aat cac    2163
Ser Ala Phe Ala Asn Phe Gly Ala Phe Gln Gln Gln Gln Gln Asn His
620                 625                 630 agc aat aat aac aat aat agc tcg tcg gca ttc gac ttg ttt caa        2208
Ser Asn Asn Asn Asn Asn Ser Ser Ser Ala Phe Asp Leu Phe Gln
635                 640                 645 tgatatttt tagcctaatt taacccaacc aacctactac ccaaaatgtc cactctcaca   2268
ttcacatttc cacgatcgct aaacttgtca gttctatata ttatttacgt tttcctttcc  2328
ccttgctgta caaagtttgc gacacgtgca atttgtttct aaattcgttg ttaaacaatt  2388 taccccgat gcaattttcc ggatcaaacc cattaattcc acatccgtcc tgatcgtcca   2448
ctcggaattt gaaagtcgtc atcaaatgca atacacagag tagttgaata atggttgtac  2508
taaacggatt cgttagcaca acgcgcggac ggacggctga gcgatccaac attgaaattg  2568
ttaaacaaaa tactacacgt aataaaatca aacaatttta gcaatagtta acgttacgat  2628
```

```
gtgtctgtat ataaattgaa tgtaaagcaa atatgaaata taaaacaatt gaaaccaata    2688
aaaaaaaaaa aaaaaaa                                                    2705
```

<210> SEQ ID NO 4
<211> LENGTH: 649
<212> TYPE: PRT
<213> ORGANISM: Drosophila melanogaster

<400> SEQUENCE: 4

```
Met Val Asp Lys Phe Ile Ser Met Trp Lys Val Arg Glu Leu Ala Asp
1               5                   10                  15

Lys Val Thr Asn Val Val Met Asn Tyr Thr Glu Thr Glu Gly Lys Val
            20                  25                  30

Arg Glu Ala Thr Asn Asp Asp Pro Trp Gly Pro Thr Gly Pro Leu Met
        35                  40                  45

Gln Glu Leu Ala Tyr Ser Thr Phe Ser Tyr Glu Thr Phe Pro Glu Val
    50                  55                  60

Met Ser Met Leu Trp Lys Arg Met Leu Gln Asp Asn Lys Thr Asn Trp
65                  70                  75                  80

Arg Arg Thr Tyr Lys Ser Leu Leu Leu Asn Tyr Leu Val Arg Asn
                85                  90                  95

Gly Ser Glu Arg Val Val Thr Ser Ser Arg Glu His Ile Tyr Asp Leu
            100                 105                 110

Arg Ser Leu Glu Asn Tyr Thr Phe Thr Asp Glu Gly Gly Lys Asp Gln
        115                 120                 125

Gly Ile Asn Val Arg His Lys Val Arg Glu Leu Ile Asp Phe Ile Gln
    130                 135                 140

Asp Asp Asp Arg Leu Arg Glu Glu Arg Lys Lys Ala Lys Lys Asn Lys
145                 150                 155                 160

Asp Lys Tyr Ile Gly Met Ser Ser Asp Ala Met Gly Met Arg Ser Gly
                165                 170                 175

Gly Tyr Ser Gly Tyr Ser Gly Gly Ser Gly Gly Gly Gly Gly Gly Ser
            180                 185                 190

Gly Gly Tyr Asn Asp Gly Asp Tyr Arg Ser Ser Arg Gly Asp Asn Trp
        195                 200                 205

Tyr Ser Asp Lys Ser Ala Asp Lys Asp Arg Tyr Glu Asp Asp Thr
    210                 215                 220

His Tyr Asp Gly Glu Arg Glu Gly Ser Asp Ser Asp Ser Pro Ser Pro
225                 230                 235                 240

Arg Arg Asn Tyr Arg Tyr Asn Asp Arg Ala Ser Pro Ala Glu Val Ala
                245                 250                 255

Ser Glu Ala Lys Pro Ser Ser Leu Asn Met Asn Ile Arg Ser Lys Thr
            260                 265                 270

Val Ser Ser Pro Val Ser Lys Gln Pro Thr Ser Thr Ala Ser Ala Lys
        275                 280                 285

Pro Ala Leu Ser Gln Lys Lys Ile Asp Leu Gly Ala Ala Ala Asn Phe
    290                 295                 300

Gly Lys Pro Ala Pro Gly Gly Ala Ala Gly Ile His Ser Pro Thr His
305                 310                 315                 320

Arg Asp Thr Pro Thr Ser Val Asp Leu Met Gly Gly Ala Ser Pro Ser
                325                 330                 335

Pro Ser Thr Ser Lys Ala Asn Asn Asn Thr Gln Ser Asn Asn Asn Asp
            340                 345                 350

Leu Leu Asp Asp Leu Phe Lys Thr Cys Ser Pro Pro Pro Gly Gln Glu
```

-continued

```
                 355                 360                 365
Lys Thr Leu Asn Ser Ala Ala Val Ile Val Asp Asp Asp Asp Phe
    370                 375                 380

Asn Pro Arg Ala Ser Asp Ala Ser Gln Gln Glu Phe Gly Asp Phe Ala
385                 390                 395                 400

Ser Ala Phe Gly Gln Pro Ser Ala Gly Ser Thr Ile Ser Glu Pro Pro
                405                 410                 415

Ser Thr Gly Leu Val Pro Ala Ala Asn Asp Glu Phe Ala Asp Phe Ala
                420                 425                 430

Ala Phe Gln Gly Ser Thr Thr Ser Thr Ser Ala Leu Asp Gly Asn Leu
            435                 440                 445

Leu Lys Thr Ala Thr Pro Ala Asn Asp Ser Phe Asp Leu Phe Asn Ser
450                 455                 460

Ala Pro Thr Ser Thr Ala Ala Thr Thr Ala Thr Asp Leu Leu Ala
465                 470                 475                 480

Gly Leu Gly Asp Leu Ser Ile His Gln Ser Met Pro Met Asp Asn Met
                485                 490                 495

Met Pro Pro Ile Pro Ala Val Thr Gly Asn Asn Leu Leu Gln Pro Met
                500                 505                 510

Ser Val Thr Asn Asn Asn Asn Thr Asn Gly Gly Ala Val Pro Ala
            515                 520                 525

Ala Ala Ser Val Gln Ser Thr Ala Val Gly Ala Thr Trp Ser Gly Asp
530                 535                 540

Leu Lys Gly Gly Lys Met Asn Ile Asp Leu Asp Asn Leu Leu Met Ser
545                 550                 555                 560

Lys Ser Gly Lys Pro Ser Ala Pro Ala Pro Ser Met Asn Ala Leu Lys
                565                 570                 575

Thr Asn Ser Pro Ala Lys Ala Pro Leu Asn Val Gln Thr Gly Gly Gly
                580                 585                 590

Phe Pro Gly Leu Ser Pro Met Thr Ser Pro Asn Ile Phe Gly Ala Pro
            595                 600                 605

Ala Pro Gln Gln Ser Ile Pro Gln Asn Gln Ser Ala Phe Ala Asn Phe
610                 615                 620

Gly Ala Phe Gln Gln Gln Gln Gln Asn His Ser Asn Asn Asn Asn
625                 630                 635                 640

Ser Ser Ser Ala Phe Asp Leu Phe Gln
                645

<210> SEQ ID NO 5
<211> LENGTH: 643
<212> TYPE: PRT
<213> ORGANISM: Homo sapiens

<400> SEQUENCE: 5

Met Leu Asn Met Trp Lys Val Arg Glu Leu Val Asp Lys Ala Thr Asn
1               5                   10                  15

Val Val Met Asn Tyr Ser Glu Ile Glu Ser Lys Val Arg Glu Ala Thr
                20                  25                  30

Asn Asp Asp Pro Trp Gly Pro Ser Gly Gln Leu Met Gly Glu Ile Ala
            35                  40                  45

Lys Ala Thr Phe Met Tyr Glu Gln Phe Pro Glu Leu Met Asn Met Leu
    50                  55                  60

Trp Ser Arg Met Leu Lys Asp Asn Lys Lys Asn Trp Arg Arg Val Tyr
65                  70                  75                  80
```

-continued

```
Lys Ser Leu Leu Leu Leu Ala Tyr Leu Ile Arg Asn Gly Ser Glu Arg
                85                  90                  95

Val Val Thr Ser Ala Arg Glu His Ile Tyr Asp Leu Arg Ser Leu Glu
            100                 105                 110

Asn Tyr His Phe Val Asp Glu His Gly Lys Asp Gln Gly Ile Asn Ile
        115                 120                 125

Arg Gln Lys Val Lys Glu Leu Val Glu Phe Ala Gln Asp Asp Asp Arg
    130                 135                 140

Leu Arg Glu Glu Arg Lys Lys Ala Lys Asn Lys Asp Lys Tyr Val
145                 150                 155                 160

Gly Val Ser Ser Asp Ser Val Gly Gly Phe Arg Tyr Ser Glu Arg Tyr
                165                 170                 175

Asp Pro Glu Pro Lys Ser Lys Trp Asp Glu Glu Trp Asp Lys Asn Lys
            180                 185                 190

Ser Ala Phe Pro Phe Ser Asp Lys Leu Gly Glu Leu Ser Asp Lys Ile
        195                 200                 205

Gly Ser Thr Ile Asp Asp Thr Ile Ser Lys Phe Arg Arg Lys Asp Arg
    210                 215                 220

Glu Asp Ser Pro Glu Arg Cys Ser Asp Ser Glu Glu Lys Lys Ala
225                 230                 235                 240

Arg Arg Gly Arg Ser Pro Lys Gly Glu Phe Lys Asp Glu Glu Thr
                245                 250                 255

Val Thr Thr Lys His Ile His Ile Thr Gln Ala Thr Glu Thr Thr Thr
            260                 265                 270

Thr Arg His Lys Arg Thr Ala Asn Pro Ser Lys Thr Ile Asp Leu Gly
        275                 280                 285

Ala Ala Ala His Tyr Thr Gly Asp Lys Ala Ser Pro Asp Gln Asn Ala
    290                 295                 300

Ser Thr His Thr Pro Gln Ser Ser Val Lys Thr Ser Val Pro Ser Ser
305                 310                 315                 320

Lys Ser Ser Gly Asp Leu Val Asp Leu Phe Asp Gly Thr Ser Gln Ser
                325                 330                 335

Thr Gly Gly Ser Ala Asp Leu Phe Gly Gly Phe Ala Asp Phe Gly Ser
            340                 345                 350

Ala Ala Ala Ser Gly Ser Phe Pro Ser Gln Val Thr Ala Thr Ser Gly
        355                 360                 365

Asn Gly Asp Phe Gly Asp Trp Ser Ala Phe Asn Gln Ala Pro Ser Gly
    370                 375                 380

Pro Val Ala Ser Ser Gly Glu Phe Phe Gly Ser Ala Ser Gln Pro Ala
385                 390                 395                 400

Val Glu Leu Val Ser Gly Ser Gln Ser Ala Leu Gly Pro Pro Ala
                405                 410                 415

Ala Ser Asn Ser Ser Asp Leu Phe Asp Leu Met Gly Ser Ser Gln Ala
            420                 425                 430

Thr Met Thr Ser Ser Gln Ser Met Asn Phe Ser Met Met Ser Thr Asn
        435                 440                 445

Thr Val Gly Leu Gly Leu Pro Met Ser Arg Ser Gln Pro Leu Gln Asn
    450                 455                 460

Val Ser Thr Val Leu Gln Lys Pro Asn Pro Leu Tyr Asn Gln Asn Thr
465                 470                 475                 480

Asp Met Val Gln Lys Ser Val Ser Lys Thr Leu Pro Ser Thr Trp Ser
                485                 490                 495

Asp Pro Ser Val Asn Ile Ser Leu Asp Asn Leu Leu Pro Gly Met Gln
```

-continued

|   |   |   | 500 |   |   |   | 505 |   |   |   | 510 |   |   |
|---|---|---|---|---|---|---|---|---|---|---|---|---|---|
| Pro | Ser | Lys<br>515 | Pro | Gln | Gln | Pro | Ser<br>520 | Leu | Asn | Thr | Met | Ile<br>525 | Gln | Gln | Gln |
| Asn | Met | Gln<br>530 | Gln | Pro | Met | Asn<br>535 | Val | Met | Thr | Gln | Ser<br>540 | Phe | Gly | Ala | Val |
| Asn<br>545 | Leu | Ser | Ser | Pro | Ser<br>550 | Asn | Met | Leu | Pro | Val<br>555 | Arg | Pro | Gln | Thr | Asn<br>560 |
| Ala | Leu | Ile | Gly | Gly<br>565 | Pro | Met | Pro | Met | Ser<br>570 | Met | Pro | Asn | Val<br>575 | Met | Thr |
| Gly | Thr | Met | Gly<br>580 | Met | Ala | Pro | Leu | Gly<br>585 | Asn | Thr | Pro | Met | Met<br>590 | Asn | Gln |
| Ser | Met | Met<br>595 | Gly | Met | Asn | Met | Asn<br>600 | Ile | Gly | Met | Ser | Ala<br>605 | Ala | Gly | Met |
| Gly | Leu | Thr<br>610 | Gly | Thr | Met | Gly<br>615 | Met | Gly | Met | Pro | Asn<br>620 | Ile | Ala | Met | Thr |
| Ser | Gly<br>625 | Thr | Val | Gln | Pro<br>630 | Lys | Gln | Asp | Ala | Phe<br>635 | Ala | Asn | Phe | Ala | Asn<br>640 |
| Phe | Ser | Lys |

GROWTH REGULATING PROTEINS

CROSS REFERENCE TO RELATED APPLICATIONS

This application is the national stage entry of PCT/IB03/01257, filed Mar. 28, 2003, which claims priority to U.S. provisional application No. 60/368,457, filed Mar. 28, 2002, the disclosure of which is incorporated herein in its entirety.

TECHNICAL FIELD

The invention relates to a novel family of proteins having growth inhibiting activity and their diagnostic and therapeutical use.

BACKGROUND ART

Growth is intimately linked not only to normal development but also to abnormal conditions such as tumorogenesis and cancer. In spite of its importance we still know relatively little about how growth is regulated at the cellular level, at the level of tissues and organs or at the level of the entire organism. Since growth is normally associated with cell multiplication much effort in understanding mechanisms regulating growth has focused on the mechanisms of cell cycle regulation. Indeed, our knowledge of how cells progress through the cell cycle has increased substantially (Nurse 2000). The preoccupation with cell division control has led to the assumption that growth is regulated by factors that control the cell cycle. Elegant experiments in *Drosophila* imaginal discs, however, reminded us old findings in yeast, that growth regulates the cell cycle and not vice versa (Nurse 1975). In the *Drosophila* experiments it was shown that accelerating the cell cycle time in clones of cells did not stimulate net growth as measured by the area occupied by the clone, but produced more but smaller cells occupying the same area as the control clones. Conversely, slowing down the cell cycle by overexpression of the RB homolog RBF generated fewer but larger cells again occupying the same area (Neufeld, de la Cruz et al. 1998). Therefore, understanding of growth regulation during normal and abnormal development requires more than understanding cell cycle control. Understanding how growth is regulated at the cellular and tissue level will also provide novel approaches and targets for cancer therapy. Indeed, inhibitors that block cell growth such as Rapamycin are presently in clinical trial as anti-cancer drugs (Hidalgo and Rowinsky 2000). There is therefore an urgent need for means, which allow the diagnosis and the therapy of hyperproliferative diseases.

DISCLOSURE OF THE INVENTION

Hence, it is a general object of the present invention to provide a protein comprising an ENTH domain and having growth inhibiting activity.

The term ENTH (Epsin $NH_2$ Terminal Homology domain) domain as used herein describes a conserved protein domain which was first found in proteins of the epsin family. Typically, this domain is located at the N-terminus of the proteins and said domain is characterised by 16 absolutely conserved residues: N-x(11–13)-V-x2-A-T-x(34–36)-R-x(7–8)-W-R-x3-K x11-G-x-E-x15-L-x(10–11)-D-x-G-x3-R-x11-D-x7R.

In a preferred embodiment said proteins lack a NPF domain which interacts with Eps15 and lack a DPW domain which binds to the clathrin adaptor AP2.

In a further preferred embodiment said proteins have an amino acid sequence which is at least 40%, preferably 50%, more preferably 60%, even more preferably 80% and most preferably 90% identical to the amino acid sequence set forth in Seq. Id. No. 2 (human ELP), or Seq. Id. No. 5 (hELP18aa) or Seq. Id. No. 4 (*Drosophila* ELP).

In a particular preferred embodiment said protein has an amino acid sequence which is identical to the amino acid sequence of Seq. Id. No. 2 (*Homo sapiens*), Seq. Id. No. 4 (*Drosophila melanogaster*) or Seq. Id. No. 5 (*Homo sapiens* h-ELP18aa).

Another object of the present invention are nucleic acid sequences encoding a protein of the present invention. In a preferred embodiment said nucleic acid sequence is selected from the group consisting of Seq. Id. No. 1 (h-ELP) and Seq. Id. No. 3 (dELP).

Another object of the present invention is a method of determining whether a subject, e.g. a human patient, is at risk for a disorder characterized by unwanted cell proliferation or aberrant control of differentiation.

Another aspect of the present invention provides antibodies and antibody preparations specifically reactive with an epitope of an epsin like protein.

A further object of the present invention is the use of proteins and/or nucleic acids of the present invention for gene therapy purposes.

In yet another aspect the present invention relates to the use of proteins and/or nucleic acids of the present invention for the treatment of hyperproliferative diseases such as e.g. cancer.

The present invention relates in a further aspect to a vector comprising a nucleotide sequence encoding a protein of the present invention. Typically, a vector comprises the regulatory sequences required to achieve expression in a host cell and it may contain necessary sequences required for plasmid replication in order to exist in an episomal state, or it may be designed for chromosomal integration. The term regulatory sequence as used herein encompasses both the native regulatory sequence of a gene of the present invention and heterologous regulatory sequences.

Furthermore, the present invention provides a host cell transformed with a vector comprising a nucleotide sequence encoding a protein of the present invention. Any host cell being able to express a protein of the present invention can be used, e.g. bacteria, vertebrate and invertebrate cells. Said cells can e.g. be used for the production of epsin like proteins.

In a further aspect, the present invention relates to a method for the production of epsin like proteins wherein suitable host cells are transformed with a vector comprising a nucleic acid sequence encoding an epsin like protein, cultivation of said host cells under conditions allowing protein expression and isolation of the produced epsin like proteins. Any host cell being able to express a protein of the present invention can be used, e.g. bacteria, vertebrate and invertebrate cells.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 2 shows a sequence alignment of dELP (Seq. Id. No 4) and hELP (Seq. Id. No 2). Dark boxes: identical residues. Grey boxes: conserved residues;

FIG. 3 shows a Clustal W alignment of the 2 h-ELP isoforms: h-ELP (Seq. Id. No. 2) (sequence from the database) and h-ELP18aa (Seq. Id. No. 5) (sequence from EST). Identical amino acids are shown by asteriks below the alignment;

FIG. 6 shows the growth phenotypes caused by overexpression of delp in eye and wing in adult flies. A) Overexpression of dELP in the developing eye induces growth inhibiting phenotypes in the adult eye, whereas overexpression in the wing leads to a severe wing size reduction, which might also involve apoptotic effects as well. B) and D) delp UAS-lines as control. Genotypes: A) y w UAS-delp 3.15; eyGal4/+ B) y w UAS-delp 3.15; +/+ C) y w MS 1096/UAS-delp 3.15 D) y w 3.15 UAS-delp; +/+; MKRS/TM3.

MODES FOR CARRYING OUT THE INVENTION

Figures 1A, 1B:
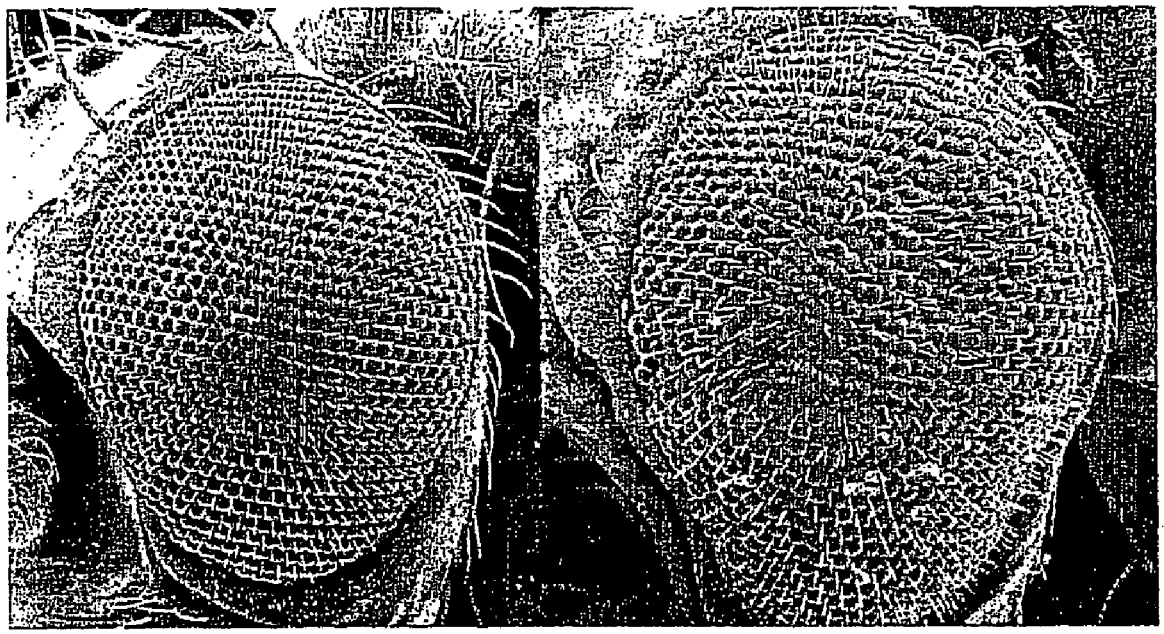
FIG. 1A shows an electro scanning micrograph of a wild-type *D. melanogaster* eye as control.
FIG. 1B shows an electro scanning micrograph of a compound eye largely composed of homozygous dELP mutant tissue. The eye displays a dramatic increase in size. The picture was taken from a female of the genotype y w ey-flp/y w; FRT82 dELP$^{4K2}$/FRT82 w+ cl3R3.

To identify genes specifically involved in growth at a cellular, tissue and organismal level, the inventors took a genetic approach in *Drosophila*. They performed a genome-wide screen for recessive mutations that interfere or promote cell growth without affecting cell differentiation. These screens were carried out by taking advantage of a tissue-specific recombination system (Newsome, Asling et al. 2000) that generates genetically mosaic flies. These flies are homozygous for randomly induced mutations in the head tissue but heterozygous for the same mutation in the body and the germ line. Mutations in genes whose products selectively promote growth (potential oncogenes) will produce flies with small heads while mutations in genes whose products exert a growth inhibiting function (potential tumor suppressor genes) results in flies with larger than normal heads. The validity of this screen to find genes involved in tumorogenesis is exemplified by the identification of mutations in *Drosophila* homologues of known oncogenes as the Target of Rapamycin TOR, Myc, Ras causing a small-head phenotype and mutations in known tumor suppressor gene homologues like PTEN, LATS and TS1 causing a big-head phenotype ((Huang, Potter et al. 1999; Oldham, Montagne et al. 2000).

Mutations in the gene described in this invention produced flies with larger than normal heads (FIG. 1) strongly suggesting an essential growth inhibiting function. The gene was later identified as being novel and named Epsin Like Protein (ELP) due to a common domain with the *Drosophila* Epsin protein. This domain, known as Epsin NH$_2$-Terminal Homology (ENTH) domain (Kay, Yamabhai et al. 1999), is found in all the Epsin family proteins (Rosenthal, Chen et al. 1999) which have been implicated in receptor mediated endocytosis and in the regulation of growth receptors (Carbone 1997; Nakashima, Morinaka et al. 1999). However, ELP is missing two essential domains of Epsin involved in endocytosis: the C-terminal NPF domain which interacts with Eps15 (Chen, Fre et al. 1998) and the DPW central motif which binds to the clathrin adaptor AP2 (Robinson P J, Liu J P,. Trends in neuroscience 1994) and Clathrin (Rosenthal, Chen et al. 1999). Since the three dimensional structure of the ENTH domain resembles the one of the Armadillo repeat, it has been postulated that this domain might also mediate nucleo-cytoplasmic shuttling (Hyman, Chen et al. 2000; Vecchi, Polo et al. 2001).

The ENTH domain has been described to bind phosphatidylinositol-4,5-bis phosphate (PIP2) (PIP2) (Itoh, Koshiba et al. 2001), the dephosphorylated form of the membrane phospholipid PI(3,4,5)P3, which plays a pivotal role in the signal propagation from membrane receptors to downstream components (Martin 2001). Thus, in analogy to proteins containing a PH domain, known to bind to and be regulated by PIP3 levels, the localization and the function of ENTH domain containing proteins might be regulated by PIP2 levels.

The fact that the growth phenotype observed in cells lacking the tumor suppressor gene LATS is very similar to the one of cells homozygous for mutations in the gene described herein indicates that ELP may also constitute a tumor suppressor gene.

In the scope of the present invention the *D. melanogaster* ELP protein and two human ELP isoforms were identified as well as the corresponding genes.

A first aspect of the present invention relates to espin like proteins (ELP) which are characterised by the presence of an ENTH domain and their growth inhibiting activity. In the scope of the present invention the epsin like proteins of *Drosopila melanogaster* and humans have been cloned and characterised.

It could be shown that DELP overexpression induces cell death in the fly wing and strongly reduce the size of the compound eye (again an indication of its negative effect on growth) and that overexpression of hElp and dElp transgenes in transheteroallelic mutant *D. melanogaster* background partially rescues homozygous mutant lethality from late larval to pupal stages. These findings prove that the *drosophila* and the human protein have the same function.

The growth inhibiting activity of said proteins indicates that the epsin like genes function as tumor suppressors.

Included within the term ELP protein are also functional fragments, variants or derivatives of any of the proteins defined hereinbefore. The proteins of the present invention can be provided as chimeric proteins for example as recombinant fusion proteins.

A "chimeric protein" or "fusion protein" is a fusion of a first amino acid sequence encoding one of the subject ELP polypeptides with a second amino acid sequence defining a domain foreign to and not substantially homologuous with any domain of one of the ELP proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-ELP-Y, wherein ELP represents a portion of the protein which is derived from one of the ELP proteins, and X and Y are independently absent or represent amino acid sequences which are not related to one of the ELP sequences in an organism, including naturally occurring mutants.

In a second aspect the present invention relates to nucleic acid sequences encoding ELP proteins. DNA sequence polymorphisms that do lead to changes in the amino acid sequence of ELP are also comprised by the present invention. One skilled in the art will appreciate that these variations in one or more nucleotides (up to about 3–5% of the nucleotides) of the nucleic acids encoding polypeptides having an activity of an ELP polypeptide may exist among individuals of a given species due to natural allelic variation. Fragments of the nucleic acids encoding an active portion of the epsin like proteins are also within the scope of the invention. As used herein, an elp gene fragment refers to a nucleic acid having fewer nucleotides than the nucleotide sequence encoding the entire amino acid sequence of ELP represented in Seq. Id No:2, Seq. Id No:4 or Seq. Id. No. 5, yet preferably encodes a peptide which retains some biological activity of the full length protein or regains some biological activity in the presence of a suitable agonist/antagonist. Nucleic acid fragments within the scope of the present invention include those capable of hybridizing under high or medium stringency conditions with nucleic acids from other species for use in screening protocols to detect and isolate other elp alleles and/or homologs, as well as those capable of hybridizing with nucleic acids from human specimens for use in detecting the presence of a nucleic acid encoding an ELP protein, including alternate isoforms, e.g. mRNA splicing variants. Nucleic acids within the scope of the invention may also contain linker sequences, modified restriction endonuclease sites and other sequences useful for molecular cloning, expression or purification of recombinant forms of the subject dispatched polypeptides.

In a further aspect the present invention relates to a method for the determination whether a subject, e.g. a human patient, is at risk for a disorder characterized by unwanted cell proliferation or aberrant control of differentiation. The method includes detecting, in a tissue sample of the subject, the presence or absence of a genetic lesion characterized by at least one mutation in an epsin like gene or the mis-expression of an epsin like gene.

To illustrate, nucleotide probes can be generated from the genes of the present invention which facilitate histological screening of intact tissue and tissue samples for the presence (or absence) of ELP encoding transcripts. The use of probes directed to ELP messages, or to genomic ELP sequences, can be used for both predictive and therapeutic evaluation of allelic mutations which might be manifest in, for example, neoplastic or hyperplastic disorders (e.g. unwanted cell growth). The oligonucleotide probes can help facilitate the determination of the molecular basis for a developmental disorder which may involve some abnormality associated with expression (or lack thereof) of an epsin like protein. For instance, variation in polypeptide synthesis can be differentiated from a mutation in a coding sequence.

E.g. by dot-blot experiments comparing ELP RNA expression in tumor tissue vs. normal tissue, significant down-regulation of ELP RNA could be found in connection with several cancers, in particular lung cancer samples, kidney cancer samples and stomach cancer samples.

In preferred embodiments, the diagnostic method can be characterized as comprising: detecting, in a tissue sample of the subject (e.g. a human patient), the presence or absence of a genetic lesion characterized by at least one of (i) a mutation of a gene encoding an epsin like protein or (ii) the mis-expression of an epsin like protein. To illustrate, such genetic lesions can be detected by ascertaining the existence of at least one of (i) a deletion of one or more nucleotides from a gene encoding an epsin like protein, (ii) an addition of one or more nucleotides to a gene encoding an epsin like protein, (iii) a substitution of one or more nucleotides of a gene encoding an epsin like protein, (iv) a gross chromosomal rearrangement of a gene encoding an epsin like protein, (v) a gross alteration in the level of a messenger RNA transcript of a gene encoding an epsin like protein, (vi) the presence of a non-wild type splicing pattern of a messenger RNA transcript of a gene encoding an epsin like protein, (vii) a non-wild type level of an epsin like protein and (viii) a mutation in the 5' untranslated region or 3' untranslated region of an elp gene.

In one aspect of the invention there is provided a probe/primer comprising an oligonucleotide containing a region of nucleotide sequence which is capable of hybridizing to a sense or antisense sequence of SEQ ID No:1, or naturally occurring mutants thereof, or 5' or 3' flanking sequences or intronic sequences naturally associated with a gene of the present invention. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR) (see, e.g., U.S. Pat. Nos. 4,683,195 and 4,683,202) or, alternatively, in a ligation chain reaction (LCR) (Landegren, Kaiser et al. 1988; Nakazawa, English et al. 1994) the later of which can be particularly useful for detecting point mutations in genes. Alternatively, immunoassays can be employed to determine the level of proteins.

In a preferred embodiment the mutation in the elp gene is located within the ENTH domain encoding region, in the 5' untranslated region of the elp gene or in the gene region right adjacent to the ENTH domain.

Another aspect of the present invention provides antibodies and antibody preparations specifically reactive with an epitope of an epsin like protein.

For example, by using immunogens derived from ELP proteins, e.g. based on the cDNA sequences, anti-protein/anti-peptide antisera or monoclonal antibodies can be made by standard protocols (See, for example, (Harlow and Lane 1988)). A mammal, such as a mouse, a hamster or rabbit can be immunized with an immunogenic form of the peptide (e.g., a vertebrate dispatched polypeptide or an antigenic fragment which is capable of eliciting an antibody response). Techniques for conferring immunogenicity on a protein or peptide include conjugation to carriers or other techniques well known in the art. An immunogenic portion of an ELP protein can be administered in the presence of adjuvant. The progress of immunization can be monitored by detection of antibody titers in plasma or serum. Standard ELISA or other immunoassays can be used with the immunogen as antigen to assess the levels of antibodies.

In a preferred embodiment, the antibodies are immunospecific for antigenic determinants of an ELP protein of a vertebrate organism, such as a mammal. Following immunization of an animal with an antigenic preparation of an ELP protein, anti-ELP antisera can be obtained and, if desired, polyclonal anti-ELP antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by (Kohler and Milstein 1975)), the human B cell hybridoma technique (Kozbar 1983), and the EBV-hybridoma technique to produce human monoclonal antibodies (Cole 1985). Hybridoma cells can be screened immunochemically for production of antibodies specifically reactive with an ELP protein and monoclonal antibodies isolated from a culture comprising such hybridoma cells.

The term antibody as used herein is intended to include fragments thereof which are also specifically reactive with one of the ELP polypeptides. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for an ELP protein conferred by at least one CDR region of the antibody.

Both monoclonal and polyclonal antibodies (Ab) directed against ELP polypeptides, or ELP variants, and antibody fragments such as Fab and F(ab)$_2$, can be used to block the action of one or more ELP proteins and allow the study of the role of these proteins in, for example, embryogenesis and/or maintenance of differential tissue. In a similar approach, hybridomas producing anti-ELP monoclonal antibodies, or biodegradable gels in which anti-ELP antibodies are suspended, can be implanted at a site proximal or within the area at which ELP action is intended to be blocked. Experiments of this nature can aid in deciphering the role of this and other factors that may be involved in growth regulation. The antibodies are as well suitable as tools for the use in diagnostic assays for the identification of diseases associated with ELP proteins or a predisposition thereof e.g. by detecting reduced or enhanced Elp protein expression, by detecting a cellular mislocalisation of an ELP protein or by detecting aberrant ELP proteins in a tissue or body fluid sample e.g. blood, of an individual. Said aberrant forms of ELP protein can e.g. be the result of an incomplete or different splicing and lead to shorter or longer ELP proteins with enhanced or reduced or different activity than the wildtype ELP protein. Furthermore, said aberrant ELP protein forms can be chimeric proteins wherein full length ELP protein or fragments thereof are fused to another protein or fragments thereof. Said chimeric protein can e.g. have arisen From a deletion between two genes or be the result of a genomic rearrangement. The man skilled in the art knows suitable methods for the detection of proteins using antibodies in a tissue and/or body fluid sample. Said methods include but are not limited to Western blots, Enzyme Linked Immunosorbent Assay ("ELISA"), cell-based ELISA, immunoprecipitations, slot or dot blots, radioimmunoassays, and fluorescent immunoassays.

In another aspect the present invention relates to the use of proteins and/or nucleic acids of the present invention (whether full-length or a desirable fragment) for the gene therapy of hyperproliferative diseases associated with ELP. An appropriate vector for delivery may be readily selected by one of skill in the art. Gene therapy vectors are readily available from a variety of sources, and include, e.g., adeno-associated virus [International patent application No. PCT/US91/03440], adenovirus vectors (Ishibashi, Brown et al. 1993; Kay, Landen et al. 1994), or other viral vectors, e.g., various poxviruses, vaccinia, etc. Methods for insertion of a desired gene, e.g., BAP-1, and obtaining in vivo expression of the encoded protein, are well known to those of skill in the art.

The proteins and/or nucleic acids of the present invention are as well suitable for the treatment of hyperproliferative diseases e.g. in the form of a pharmaceutical preparation. The pharmaceutical preparations can—if desired—be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

The proteins may be administered by injection (i.e., subcutaneous, intravenous, intramuscular, intratumoral, intraperitoneal, preferably intramuscular), oral administration, inhalation, transdermal application, topical administration or rectal administration, preferably by injection, transdermal or topical administration. Depending on the route of administration, the peptides in the pharmaceutical compositions may be coated in a material to protect them from the action of certain enzymes. A person skilled in the art would be familiar with the coating which would be suitable for delivery of the peptide to a particular site. Organic substances may also be included in the compositions to prolong the pharmacologic actions of the peptides. Examples of such organic substances include non-antigenic gelatin, carboxymethylcellulose, sulfonate or phosphate ester of alginic acid, dextran, polyethylene glycol and other glycols, phytic acid, polyglutamic acid, and protamine.

For therapy purposes, an active ELP peptide or a fragment thereof can as well be administered in form of a conjugate with an appropriate carrier molecule. The carrier molecule allows an enhanced cellular uptake of the ELP peptide into the cell and/or the delivery of the ELP peptide to specific target cells e.g. tumor cells. Suitable carrier molecules are e.g. transferrin or viral cell-entry proteins.

The invention relates furthermore to antisense molecules which can be used to down-regulate expression of ELP molecules in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see (Wagner, Matteucci et al. 1996)).

Another aspect of the invention relates to post transcriptional silencing of elp genes by means of RNA interference (RNAi). RNAi is a form of post-transcriptional gene silencing mediated by short double stranded RNAs (dsRNA) that has been described in plants, nematode, invertebrates organisms and mammalian cell culture ((Ngo, Tschudi et al. 1998) (Vaucheret and Fagard 2001) (Kennerdell and Carthew 1998; Caplen, Fleenor et al. 2000; Elbashir, Harborth et al. 2001; Timmons, Court et al. 2001). Double stranded RNAs (dsRNA) have been shown to induce a degradation response in which single stranded RNA complementary to the short dsRNA is rapidly degraded (Montgomery and Fire 1998; Montgomery, Xu et al. 1998). RNAi can thus be used to reduce gene expression for instance in whole organisms or invertebrate and vertebrate cell lines (Kennerdell and Carthew 1998; Caplen, Fleenor et al. 2000; Clemens, Worby et al. 2000; Elbashir, Harborth et al. 2001). ELP dsRNA can be made from cDNA or genomic DNA templates, as long as most of the dsRNA corresponds to exon regions. Normally, target regions of 700 to 800 base pair are the most active. However, it is known that dsRNAs as short as 200 base pair and as long as 2000 base pairs have potent interfering activities. Both RNA strands can be synthesized simultaneously from a PCR fragment, which contains for instance a T7, SP6 or a T3 promoter on each end. This PCR fragment can be generated by amplification of ELP cDNA or genomic DNA with 2 primers containing e.g. T7-polymerase binding sites. The PCR reaction can then be performed with a suitable template containing ELP sequences. Taq polymerase gives the best yields, but another polymerase like Pfu may be used, too. The first 10 cycles should have a 40° C. annealing step, followed by 35 cycles with a 55° C. annealing step. DMSO can be added to a final concentration of 5% when needed. Phenol-chloroform extract and ethanol precipitation in $NH_4OAc$ may be used to isolate the PCR template from the reaction mix however other commercially available PCR-purification kit can be used as well. The RNA synthesis reaction can be performed in 50 µl volume with 1 µg of PCR DNA template using an appropriate RNA polymerase. The MEGAscript™ kits from Ambion work very well. The RNA becomes double-stranded during the synthesis reaction. The DNA template can be removed with RNase-free DNAase and the dsRNA can be purified by phenol-chloroform extraction and ethanol precipitation. Typical yields of RNA from 1 µg DNA template are in the 80 to 120 µg range. dsRNA can be stored as a NaOAc/ ethanol precipitate at −80° C. until immediately before use.

The quality of the dsRNA can be monitored by native agarose gel electrophoresis in TBE. Only preparations should be used in which the electrophoretic mobility of most of the RNA is shifted to the mobility expected for dsRNA (very close to duplex DNA mobility) of the appropriate length. To reduce ELP expression in mammalian cells, short 20–23mer dsRNA should be preferentially used (Elbashir, Harborth et al. 2001; Elbashir, Lendeckel et al. 2001). Such short dsRNA have a 3'-overhang as described in (Elbashir, Harborth et al. 2001) and can be synthesized in vitro by standard methods.

Several methods to introduce dsRNA into cells can be found in the literature and said methods are known to a man skilled in the art.

The invention is now further illustrated by means of examples.

These examples are provided merely as illustrative of various aspects of the invention and should not be considered to limit the invention in any way.

Experimental Part

To identify genes specifically involved in growth at a cellular, tissue and organismal level, the inventors took a genetic approach in *Drosophila*. They performed a genome-wide screen for recessive mutations that interfere or promote cell growth without affecting cell differentiation. These screens were carried out by taking advantage of a tissue-specific recombination systems (Newsome, Asling et al. 2000) that generates genetically mosaic flies. These flies are homozygous for randomly induced mutations in the head tissue but heterozygous for the same mutation in the body and the germ line. Mutations in genes whose products selectively promote growth (oncogenes) will produce flies with small heads while mutations in genes whose products exert a growth inhibiting function (tumor suppressor genes) results in flies with larger than normal heads. The validity of this screen is exemplified by the identification of mutations in the gene coding for the Target of Rapamycin (TOR) causing a small-head phenotype and mutations in the gene encoding the tumor suppressor gene PTEN causing a big-head phenotype (Huang, Potter et al. 1999; Oldham, Montagne et al. 2000).

EXAMPLE I

Pinhead Screening

Mutations in components of the insulin receptor signaling pathway impair cellular growth in a cell-autonomous fashion (Bohni, Riesgo-Escovar et al. 1999; Verdu, Buratovich et al. 1999; Weinkove, Neufeld et al. 1999; Brogiolo, Stocker et al. 2001). Clones of mutant cells bear a severe growth disadvantage and remain small compared to their wild-type sister clones. If mitotic recombination is forced to occur by the constant supply of flp recombinase and the sister clone gets eliminated by means of a cell-lethal mutation, these clones can, however, cover substantial fractions of whole organs. Driving the expression of the flp recombinase under the control of eyeless regulatory sequences results in the formation of tissue-specific clones in the eye imaginal disc solely. In combination with a cell-lethal mutation on the homologous chromosome, this system allows for the generation of eyes and head capsules largely composed of cells that are homozygous mutant for the gene of interest (Newsome, Asling et al. 2000). Such mosaic flies that lack the function of the IRS homolog Chico or of the insulin receptor (Inr) specifically in the descendants of the eye imaginal disc show a very characteristic phenotype. While their bodies are of normal size, their eyes and heads are dramatically reduced (Bohni, Riesgo-Escovar et al. 1999; Brogiolo, Stocker et al. 2001). In order to identify mutations in growth-modulating genes based on similar phenotypes, ales carrying target sites for the flp recombinase near the base of the right arm of the 3rd chromosome (82FRT) were subjected to EMS mutagenesis and crossed to females that brought in four elements: the source of the recombinase (ey-flp), FRT sites at the corresponding position, a dominant eye marker (w+) and a cell-lethal mutation (cl3R3). In the mosaic flies of the F1 generation, the effects of homozygosity for newly induce mutations on 3R can be observed in the heads and the eyes. The presence of homozygous mutant tissue can easily be visualized by the loss of the pigment marker w+ resulting in white eye tissue.

Screening of Mosaic Flies

Males carrying FRT sites on the right arm of chromosome 3 (FRT82; (Xu and Rubin 1993)) were fed with 33 mM EMS according to standard protocols and crossed to females of the genotype y w ey-flp; FRT82 w+ cl3R3/TM6B y+. cl3R3 is a recessive cell-lethal mutation that has been generated on the FRT82 w+ chromosome (Newsome, Asling et al. 2000). Half of the F1 progeny was of the genotype y w ey-flp/+ or Y; FRT82 */FRT82 w+ cl3R3 and was scored for eyes and heads of abnormal size. Positives were re-crossed to y w ey-flp; FRT82 w+ cl3R3/TM6B y+ to check for germline transmission. About 50'000 mosaic flies were screened to reach saturation, and 69 mutations that caused a big head phenotype were established.

Complementation Group Analysis 52 of the 69 mutations causing a big head phenotype fell into nine complementation groups. A complementation group is defined by a number of at least two alleles which in any pairwise combination fail to complement the lethality associated with homozygosity of each of the alleles. Mutations belonging to four of these complementation groups resulted in a hyperproliferative phenotype: the supernumerary ommatidia caused the formation of folds that gave the eyes a tumorous appearance (FIG. 1, right panel).

Meiotic and SNP Mapping

One of the four complementation groups showing a hyperproliferative phenotype consisted of four alleles. One representative allele was mapped meiotically using following genetic markers: a mini-w+ bearing P-element at cytological position 87E, a w+ bearing P-element at 90E, and a y+ bearing P-element at 96E ((Xu and Rubin 1993)). The rough map position was confirmed and refined by complementation analysis using deficiencies within the same region. More restrictive mapping was done by assessing the frequency of recombination between alleles and nearby marked P-element insertions. The P-elements used for the mapping were EP(3)0738 (94A1-2), 1(3)j5B5 (94A1-2) and 1(3)L3560 (94A5-7). In this manner the genetic position of the mutations could be narrowed down to chromosome position 94A in close proximity to the P-element insertion 1 (3) L3560.

The genetic analysis positioned the site of mutation in a 300 kbp interval of roughly 120 kb within scaffold AE003738 (nucleotides 344000–464000). To specifically determine the molecular site of the mutation recombinants were mapped using SNPs as molecular markers in that specific region. SNPs were resolved by denaturing HPLC analysis using the WAVE system ((Underhill, Jin et al. 1996)). The site of mutation was narrowed down to an interval of 30 kbp. The precise location of a mutation was identified by analysis of candidate genes using the WAVE system and subsequent sequencing.

EXAMPLE II

Expression of ELP in *Drosophila melanogaster*

A specific transgene can be expressed in *Drosophila* in the whole organism, in a particular organ or in a specific cell type, during the whole life or only at a specific developmental stage, and at different levels. An overview of the standard methods used in *Drosophila genetics* can be found in [Brand, 1993; Perrimon, 1998; Perrimon, 1998]. As a putative tumor suppressor gene, overexpression of wild-type or mutant ELP protein is expected to interfere with growth. To proof this hypotesis, transgenic flies carrying UAS transgenes encoding wild-type *Drosophila* ELP protein were crossed with flies having Gal4 expressed under the control of different tissue-specific promoters (FIG. 6 and Table 2). The GAL4-driven constructs include but are not limited to eyeless-Gal4, vestigal-Gal4, MS1096-Gal4 (Capdevila and Guerrero 1994). In a similar way, it is possible to test the function of mutants proteins with amino acid substitutions or internal deletions.

TABLE 2

Overexpression of DELP in different tissues.

| | GMRGal4 | eyGal4 | C765Gal4 | MS1096 | apGal4 | armGal4 | daGal4 |
|---|---|---|---|---|---|---|---|
| 3.15 on X | rough eye | vs eye omm #↓ | subviable, +/− veins | subviable; ru. wings | lethal | no vis. ph. | lethal |
| 3.24 B on III$^{rd}$ | rough eye | vs eye omm #↓ | subviable, +/− veins | subviable; ru. wings | lethal | no vis. ph. | lethal |

Transgenic animals bearing two independent insertions of delp were crossed to respective GAL4-sources indicated in the first row to overexpress dELP in a variety of tissues.
Abbreviations:
vs eye omm #↓: very small eyes, ommatidia number reduced;
+/− veins: additional or lost veins in wing;
ru. wings: rudimentary wings, very small in size;
no vis. ph.: no visible phenotype With the visible phenotype obtained by overexpressing wild-type (as in FIG. 6) or likely mutant ELP, this system can be used to perform structure/function analysis of the ELP protein. Such a phenotype can also be used to screen for dominant or recessive loss of function mutations in other genes resulting in a suppression of the phenotype. Alternatively, using the Enhancer-Promoter (EP) Element (Rorth 1996) a screen for genes that supress the phenotype when they are overexpressed can be conducted. In this case, overexpression of a random gene is caused by the integration of an EP element into the 5' end of this gene.

EXAMPLE III

Cloning of the Human Homologue

Human ELP (hELP) (Seq. Id. No. 1,2,5) was identified by searching the public sequence database for predicted coding sequences and expressed sequence tags (ESTs) having homology to the sequence of DELP using the program Blastp (http://www.ch.embnet.org/software/aBLAST.html). dELP showed statistically significant similarity to a predicted gene on chromosome V and to several ESTs. The hELP full-length cDNA was obtained from the full-length human cDNA clone collection from Resgen (Accession AL529948 Clone ID CS0DD005YJ09 Library LTI_NFL001_NBC4). This collection of cDNAs was derived from libraries constructed using oligodT primer and Superscript II reverse transcriptase. After the assembly process, the sequence was verified by crosschecking with genomic DNA sequences and the publicly available data.

To confirm the functional homology between *Drosophila* and human ELP, human and *Drosophila* full-length ELP cDNA were cloned into a *Drosophila* expression vector like the pUAS transformation vector (Phelps and Brand 1998). Transgenic flies can be generated according to the method described in (Basler and Hafen 1988). The transgenes crossed into flies that are transheterozygous for anyone of two elp mutant alleles and also contain a Gal-4 transgene allowing ubiquitous or tissue and/or stage-specific expression of the UAS-transgenes. The Gal4 transgenes include but are not limited to the actin-Gal4, tubulin-Gal4, and heatshock-Gal4. As shown in Table 1 ubiquitous expression of *Drosophila* or the human transgene did at least partially rescue the lethality associated with the transheterozygosity of the elp mutant alleles from late larval to pupal stages. This demonstrates that the help gene is the functional homologue of the *Drosophila* elp gene (see FIG. 6).

TABLE 1

Rescue analysis of delp-alleles by ubiquitous ELP overexpression.

| genotype abbreviated | Rescue at 25° C. | Rescue at 18° C. |
|---|---|---|
| 5.20d/hsGal4; Delp$^{1U1}$/Delp$^{2W2}$ | non Tb pupae | — |
| 2.4a/armGal4; Delp$^{1U1}$/Delp$^{2W2}$ | 1 non Tb pupa | no progeny |
| 2.4a/hsGal4; Delp$^{1G1}$/Delp$^{4K2}$ | small non Tb pupae | non Tb pupae |
| 2.4a/Act5CGal4; Delp$^{1U1}$/Delp$^{2W2}$ | very few offspring | — |
| 5.20d/armGal4; Delp$^{1G1}$/Delp$^{4K2}$ | small non Tb pupae | — |
| 5.20d/armGal4; Delp$^{1U1}$/Delp$^{2W2}$ | small non Tb pupae | small non Tb pupae |
| 5.20d/Act5CGal4; Delp$^{1G1}$/Delp$^{4K2}$ | MKRS/elp y appear | MKRS/elp y appear |

UASElp-transgenes were used to overexpress Elp in transheteroallelic homozygous mutant situation.
UAS-Elp-transgenes used: 2.4a: UAS-hElp18aa; 5.20d: UAS-DElp-ENTH.
Elp-alleles used: Delp$^{1G1}$: V266F-mutation; Delp$^{4K2}$: E27G-mutation; Delp$^{1U1}$: transition in 5'UTR; Delp$^{2W2}$: transition in 5'UTR. GAL4-sources used: armGal4: armadillo-Gal4; hsGal4: heatshock-Gal4; Act5CGal4: Actin5C-Gal4. UAS-transgenes and Gal4-strains were marked by w+.

Alternatively, the *Drosophila* and human full-length cDNA can be inserted in the following sequence in a transformation vector containing a tubulin promoter: tubulin promoter—FRT—cDNA STOP—FRT—Gal4 (abbreviated: tub:>cDNA>Gal4). In this way, the rescue transgene is directly controlled by the tubulin promoter resulting in lower and possibly more physiological levels of ELP expression than with the Gal4 system. Furthermore, in an ELP mutant background the elp cDNA can be excised in clones of cell by expressing the FLP recombinase either under a heat-shock inducible promoter of under a tissue specific promoter. The mutant cells generated in this way can be recognized by means of a UAS-GFP reporter since in these cells GAL4 is driven by the tubulin promoter. This method has been recently described by Kramps et al. (Cell 109: 47–60, 2002).

EXAMPLE IV

Use of ELP DNA as a Hybridization Probe

The following method describes use of a non-repetitive nucleotide sequence of elp as a hybridization probe. The method can be applied to screen for ELP homologs as well. DNA comprising the sequence of elp (as shown in Seq. Id. No. 1 and 3) is employed as probe to screen for homolog DNAs (such as those included in cDNA or genomic libraries).

Hybridization and washing of the filters containing either library DNAs is performed under, standard high stringency conditions (Sambrook, Fritsch et al. 1989). Positive clones can be used to further screen larger cDNA library platings. Representative cDNA-clones are subsequently cloned into pBluescript (pBS, Stratagene) or similar cloning vectors, and sequenced.

EXAMPLE V

Use of elp as a Hybridization Probe for In Situ Hybridization

Figure 4A:
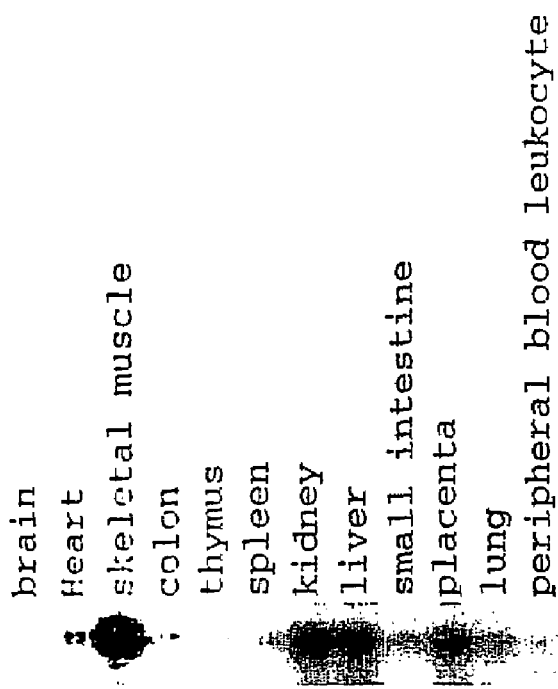
FIG. 4A shows expression of h-ELP transcripts in human tissue.
Figure 4B:
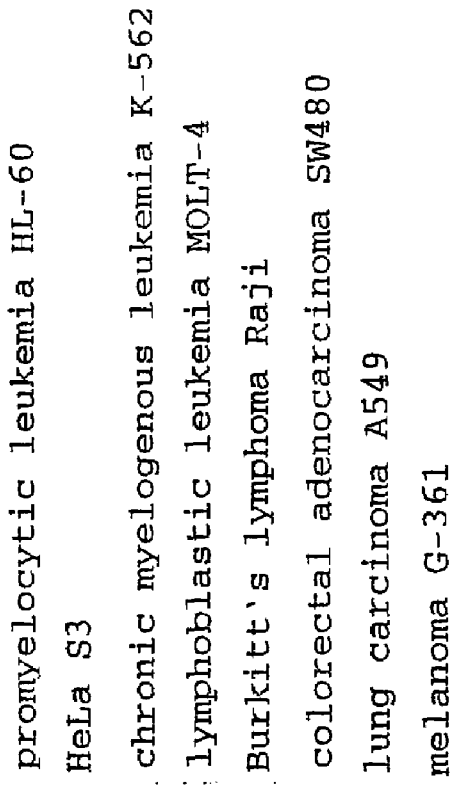
FIG. 4B shows expression of h-ELP transcripts in multiple cell lines. Northern blots (Clonetech) were hybridized with a 32P labeled h-ELP probe (nucleotides 751 to 1951). Hybridization was with ExpressHyb (Clonetech) at 68° C. with a final washing using 0.1×SSC and 0.1% SDS at 68° C. for 10 minutes.

In situ hybridization of *Drosophila* elp mRNA can be performed in embryo as described in (Tautz and Pfeifle 1989). However, with small modifications it can also be used to detect any mRNA transcript in *Drosophila* or vertebrate tissue sections. Labeled RNA probes can be prepared from linearized elp cDNA, or a fragment thereof, e.g. using the DIG RNA labeling Kit (SP6/T7) (Boehringer Mannheim) or $^{32}$P-labeling following the manufacturer's recommendations. A similar method can be used with help as a hybridization probe to screen human tissues (see FIGS. 4, and 5).

EXAMPLE VI

Expression of ELP Proteins in *E. coli*

The following method describes recombinant expression of ELP in bacterial cells. Alternatively, recombinant proteins can be produced and isolated from insect and mammalian cells (Sambrook, Fritsch et al. 1989). DNA encoding full-length or a truncated ELP form is fused downstream of an epitope tag or glutathione-S-transferase (GST) cDNA and a thrombin cleavage site contained within an inducible bacterial expression vector. Such epitope tags include poly-his, S-protein, thioredoxin, and immunoglobin tags. A variety of plasmids can be employed, including commercially available plasmid such as pGEX-4T (Pharmacia).

Briefly, a bacterial expression plasmid containing the ELP sequence, for instance fused to a GST-sequence is transformed by conventional methods into protease deficient *E.coli* such as BL21 (e.g. Stratagene) A bacterial colony containing the plasmid is then expanded overnight in selection medium to reach saturation. The next morning, this culture is diluted 1:100 and bacterial are allowed to grow to an optical density (OD600) of 0.6. Protein production is initiated by addition of an inducer of the promoter under which GST-ELP fusion protein is expressed. A variety of inducers can be employed depending on the expression vector used, including IPTG.

Expressed GST tagged ELP can then be purified, for instance, using affinity beads or affinity chromatography, such as glutathione beads (commercially available e.g. from Pharmacia). Extracts are prepared by lysing the Lgs-expressing bacteria in sonication buffer (10 mM Tris HCl pH 8.0, 150 mM NaCl, 1 mM EDTA, 1.5% sarkosyl, 2% Triton-X-100, 1 mM DTT and protease inhibitors), followed by short sonication on ice (e.g. 3 times 20 seconds at middle power) and centrifugation. Cleared supernatants are then incubated under gentle rotation for example with glutathione beads for 1 hrs at 4° C. Next beads are washed several time in washing buffer (20 mM Tris pH 8.0, 200 mM NaCl, 1 mM EDTA, 1 mM DTT, 1 mM MgCl2, 0.5% NP40), and finally stored in storage buffer (20 mM Tris pH 8.0, 200 mM NaCl, 1 mM EDTA, 1 mM DTT, 1 mM MgCl2, 10% glycerol, 0.5% NP40, and proteinase inhibitors). Alternatively, a His-tagged or IgG tagged ELP can be purified using Ni2+-chelate affinity chromatography or Protein A or Protein G column chromatography, respectively.

The quality of the preparations can be checked e.g. by SDS-gel electrophoresis and silver staining or Western blot.

In case the epitope tagged has to be cleaved, several methods are available depending on the presence of a cleavage site between the epitope tagged and the ELP protein. For example, it is possible to produce a GST-ELP fusion protein containing a thrombin cleavage site right before the first ELP amino acid. Briefly, a GST-ELP preparation on glutathione-affinity beads is washed several times in cleavage buffer (50 mM Tris HCl pH 7.0, 150 mM NaCl, 1 mM EDTA, 1 mM DTT). Thrombin is then added and the samples are incubated for over 16 hrs at room temperature. Supernatants are then collected and analyzed for successful cleavage of ELP from the beads by polyacrylamide gel electrophoresis and silver staining or Western blot. The purified proteins can be used e.g. to generate anti-ELP antibodies as described in (Harlow and Lane 1988).

EXAMPLE VII

Protein-protein Interactions Involving ELP

An in vitro co-immunoprecipitation assay can be performed to find or confirm ELP interaction partners. For instance, HEK293 cells at 50% confluence are transfected by a lipofection method. For this purpose, mammalian expression vectors containing cDNA encoding for tagged ELP and potential interaction partners are combined with Lipofectamine transfection reagent (Life Technologies, Inc.) following the manufacturer recommendations, and overlaid onto monolayers of cells. Cells are lysed 25 hrs after transfection in co-IP buffer (20 mM Tris HCl pH 7.5, 140 mM NaCl, 1.5 mM MgCl2, 1 mM EDTA, 1 mM DTT, 1% Triton-X100, 10% glycerol, 1 mM Natrium vanadate, 50 mM NaF, and protease inhibitors). Immunoprecipitations are performed in co-IP buffer using anti-tag antibodies (e.g. anti-HA, clone 3F10, Boehringer Mannheim) conjugated to protein G-agarose (Boehringer Mannheim). Control immunoprecipitations are performed using rat or mouse IgG (Sigma-Aldrich). After 3 hrs incubation at 4° C., beads are washed 4 times in washing buffer (20 mM Tris HCl pH 7.5, 140 mM NaCl, 1.5 mM MgCl2, 1 mM EDTA, 1 mM DTT, 1% Triton-X100, 1 mM Natrium vanadate, 50 mM NaF) and resuspended in 25 µl of Laemmli buffer. Immune complexes are analyzed by SDS-PAGE/immunoblot assay using anti-ELP polyclonal antibodies provided by the invention or anti-tag antibodies, followed by horseradish peroxidase conjugated secondary antibody (Amersham Pharmacia Biotech). Detection can be performed using an enhanced chemiluminescence detection method (e.g. ECL, Amersham Pharmacia Biotech).

A GST-fusion protein in vitro binding assay can be performed e.g. to map binding domains, confirm an interaction partner or find additional interacting proteins. For this purpose, proteins are in vitro translated (IVT) using reticulocyte lysates (TNT-lysates, Promega Corporation) containing [35S] methionine following the instructions provided by the manufacturer. Glutathione S-transferase (GST) fusion proteins, produced as illustrated in the Example VI, are immobilized on glutathione-Sepharose and blocked in binding buffer (20 mM Tris pH 8.0, 200 mM NaCl, 1 nM EDTA, 1 mM DTT, 1 mM MgCl2, 10% glycerol, 0.5% NP40, 0.05% BSA, and proteinase inhibitors) for 45 min. Two µg of immobilized GST proteins are then incubated for 1.5 hrs with 0.5–4 µl of IVT proteins in binding buffer. The beads are washed four times in washing buffer (20 mM Tris pH 8.0, 200 mM NaCl, 1 mM EDTA, 1 mM DTT, 1 mM MgCl2, 0.5% NP40) and boiled in Laemmli SDS sample buffer. The use of equivalent amounts of intact GST fusion proteins and successful IVT of the cDNAs have to be confirmed by SDS-PAGE analysis using Coomassie staining or autoradiography, respectively.

A yeast two hybrid assay can additionally be performed to confirm the results of the in vitro binding assays described above or to screen a cDNA library for new interaction partners (Fields and Sternglanz 1994). To confirm a specific binding or to map the binding region between ELP and an interaction partner, the desired cDNAs are subcloned into appropriate yeast expression vectors that link them either to a Lex DNA binding domain (e.g. pLexA, Clontech) or an acidic activation domain (e.g. pGJ4-5, Clontech). The appropriate pair of plasmids is then transformed together with a reporter plasmid (e.g. pSH18-34, Clontech) into an appropriate yeast strain (e.g. EGY48) by the lithium acetate-polyethylene glycol method and grown on selective media (Sambrook, Fritsch et al. 1989). Transformants are analyzed for reporter gene activity as described by the manufacturer of the vector-reporter plasmid used. To establish reproducibility the interactions is tested in both directions.

To isolate novel ELP-binding proteins (Bartel, Fields "The Yeast two-Hybrid System" Oxford UP, 1997) an appropriate yeast strain is transformed with a beta-Galactosidase reporter plasmid, a yeast expression vector containing ELP cDNA, or parts thereof, fused to the LexA DNA-binding domain sequence ("bait vector") and a second yeast expression vector containing a transcriptional activation domain fused to a collection of cDNA sequences ("prey vector" library, e.g. RFLY1 0–12 h embryo library, described in PNAS 93, 3011ff.). The triple transformants containing the reporter plasmid, and the bait and prey vectors are then grown on selective media, and selected for interaction-dependent activation of the auxotrophic and beta-Galactosidase reporters. From selected clones the respective prey construct is reisolated and the specificity of bait/prey-interaction is, assessed, by checking for absence of interaction with unrelated bait-constructs. Finally the confirmed interactors are sequenced and full-length cDNAs are assembled and tested again for specific interaction with the bait.

EXAMPLE VIII

Immunohistochemistry

Localization of ELP protein can be performed on *Drosophila* embryo, imaginal discs, adult tissue sections, vertebrate tumor cell lines, or vertebrate tissues using the anti-ELP antibodies provided by this invention. For instance, if a transformed cell line like HEK 293 cells (ATCC) is used, cells are seeded into polylysine-coated 8 well chambers (Nalge-Nunc Internat.) and grown overnight at 37° C. The next day, cells are fixed with 3.7% formaldehyde in PBS for 10 min, permeabilized in 0.5% Triton-X-100 for another 10 min, and blocked with a 1:1000 dilution of pre-immunoserum in 2% BSA-PBS for 1 h at RT. Cells are then incubated with a 1:2000 dilution of anti-ELP polyclonal rabbit immunoserum provided by this invention for 2 hrs at RT. The slides are washed three times for 5 min in PBS and incubated with a 1:200 dilution (v/v) of TRITC-conjugated swine anti-rabbit immunoglobulin (Dako, Inc.). The washing step is repeated before applying coverslips using Vectashield® mounting medium (Vector Laboratories, Inc.). As a positive control for specific staining part of the cells can be transfected e.g. by a lipofection method with a ELP expression plasmid, such as pcDNA3.1 (Invitrogen). Two days after transfection, control cells are stained with anti-ELP antibodies as described above.

EXAMPLE IX

RNA Interference Experiments

RNA interference (RNAi) is a form of post-transcriptional gene silencing mediated by short double stranded RNAs (dsRNA) that has been described in plants, nematode, invertebrates organisms and mammalian cell culture ((Ngo, Tschudi et al. 1998; Vaucheret and Fagard 2001) (Kennerdell and Carthew 1998; Caplen, Fleenor et al. 2000; Elbashir, Harborth et al. 2001; Timmons, Court et al. 2001). DsRNAs have been shown to induce a degradation response in which single stranded RNA complementary to the short dsRNA is rapidly degraded (Montgomery and Fire 1998; Montgomery, Xu et al. 1998). RNAi can thus be used to reduce gene expression for instance in whole organisms or invertebrate and vertebrate cell lines (Rennerdell and Carthew 1998; Caplen, Fleenor et al. 2000; Clemens, Worby et al. 2000; Elbashir, Harborth et al. 2001). Several methods to introduce dsRNA into cells can be found in the literature. By hand of an example, we describe herein the treatment of *Drosophila* cells with delp dsRNA.

ELP dsRNA Preparation

ELP dsRNA can be made from cDNA or genomic DNA templates, as long as most of the dsRNA corresponds to exon regions. Normally, target regions of 700 to 800 base pair are the most active. However, is known that dsRNAs as short as 200 base pair and as long as 2000 base pairs have potent interfering activities. Both RNA strands can be synthesized simultaneously from a PCR fragment, which contains for instance a T7, SP6 or a T3 promoter on each end. This PCR fragment can be generated by amplification of ELP cDNA or genomic DNA with 2 primers containing e.g. T7-polymerase binding sites. Primers complementary sequences should be 20 to 24 nucleotides in length with a 22 nucleotides optimum and 60° C. optimum Tm. The 5' end of each primer should correspond to e.g. a 27 nucleotides T7 promoter sequence. The PCR reaction is then performed with a suitable template containing ELP sequences. Taq polymerase gives the best yields, but another polymerase like Pfu may be used, too. The first 10 cycles should have a 40° C. annealing step, followed by 35 cycles with a 55° C. annealing step. DMSO can be added to a final concentration of 5% when needed. Phenol-chloroform extract and ethanol precipitation in NH4OAc may be used to isolate the PCR template from the reaction mix however other commercially available PCR-purification kit can be used as well. The RNA synthesis reaction can be performed in 50 µl volume with 1 µg of PCR DNA template using an appropriate RNA polymerase. The MEGAscript™ kits from Ambion work very well. The RNA becomes double-stranded during the synthesis reaction. The DNA template can be removed with RNase-free DNAase and the dsRNA can be purified by phenol-chloroform extraction and ethanol precipitation. Typical yields of RNA from 1 µg DNA template are in the 80 to 120 µg range. dsRNA is stored as a NaOAc/ethanol precipitate at −80° C. until immediately before use.

The quality of the dsRNA can be monitored by native agarose gel electrophoresis in TBE. Only preparations should be used in which the electrophoretic mobility of most of the RNA is shifted to the mobility expected for dsRNA (very close to duplex DNA mobility) of the appropriate length.

Transfection of ELP dsRNA into *Drosophila* S2 Cells

S2 cells are propagated in Schneider S2 *Drosophila* medium (GIBCO) supplemented with 10% FCS. One day before transfection one million cells are seeded into 6 well plates and grown overnight at 25° C. Cells are then transfected using the cationic lipid CellFectine (GIBCO) using an adaptation of the manufacturer's protocol. Briefly, a total of 5 µg DNA and dsRNA is complexed with 20 µl of CellFectine lipid mix in 1.2 ml serum free growth medium (e.g. DES expression medium from Invitrogen, Carlsbad, USA). The complexes are incubate for 15 minutes at RT and then added to the cells from which the normal growth medium has been replaced with 1 ml serum free medium. Four hours later 1.2 ml growth medium supplemented with 30% FCS is added to the cells. One day after transfection the medium is replaced with fresh medium containing 10% FCS. Cells can be assayed from 2 days after transfection (e.g. for ELP protein level or for Tcf transcriptional activity).

Similarly, mammalian ELP expression can be reduced using the method described in (Elbashir, Harborth et al. 2001).

EXAMPLE X

Identification and Cloning of an Alternative Help Splicing Variant and a Chimeric est Two human est isoforms of ELP were found in the public est database: a short and a long version. The short one lacks 54 bases close to the c-term, probably due to different or incomplete splicing (FIG. 3). Both isoforms were cloned by standard molecular biology techniques using gene specific primes and est/cDNA clones (short: BE615647, BE61693, BG528377; long:cDNA clone AL529948).

hElp reside in 5q, a chromosomal region frequently deleted in some types of cancer (Genomics 2000 May 15;66(1):26–34). It is postulated that, the loss of genetic material from this chromosomal region in association with a specific syndrome is suggestive of a recessive mechanism of tumorigenesis, and that the deleted chromosome bands harbor a tumor suppressor. The growth inhibitory activity of ELP indicates that ELP might be the tumor suppressor in this region.

To support this hypothesis, the inventors found by complete sequencing of one of the hELP est ordered from the public database a chimeric est composed of the C-term of h-ELP fused to AF156165, a gene discovered by mapping the 5q chromosome region (Genomics 2000 May 15;66(1): 26–34). h-ELP and AF156165 are located between the regions 5q23 and 5q33 and the 5q31 and 5q32, respectively. The chimeric est might have arisen from a deletion between the two genes and produce an incomplete ELP protein lacking the ENTH domain.

EXAMPLE XI

ELP RNA Expression in Normal vs. Tumor Tissues

Cancer Profiling Array (BD Biosciences cat. 7841-1) membranes were hybridized with 5' labeled hELP probe (nucleotides 751 to 1951). Hybridization was performed at 68° C, according to manufacturer's recommendation with a final washing using 0.2×SCC and 0.5% SDS at 68° C. for 15 min. For sample reference see BD bioscience catalog. A dot-blot showing ELP RNA expression in a set of normal versus tumor tissues is found in FIG. 5 showing expression of hELP transcript and the percentage of tumors having increased and decreased ELP expression is summarized in Table 3 below.

TABLE 3

Figure 5:
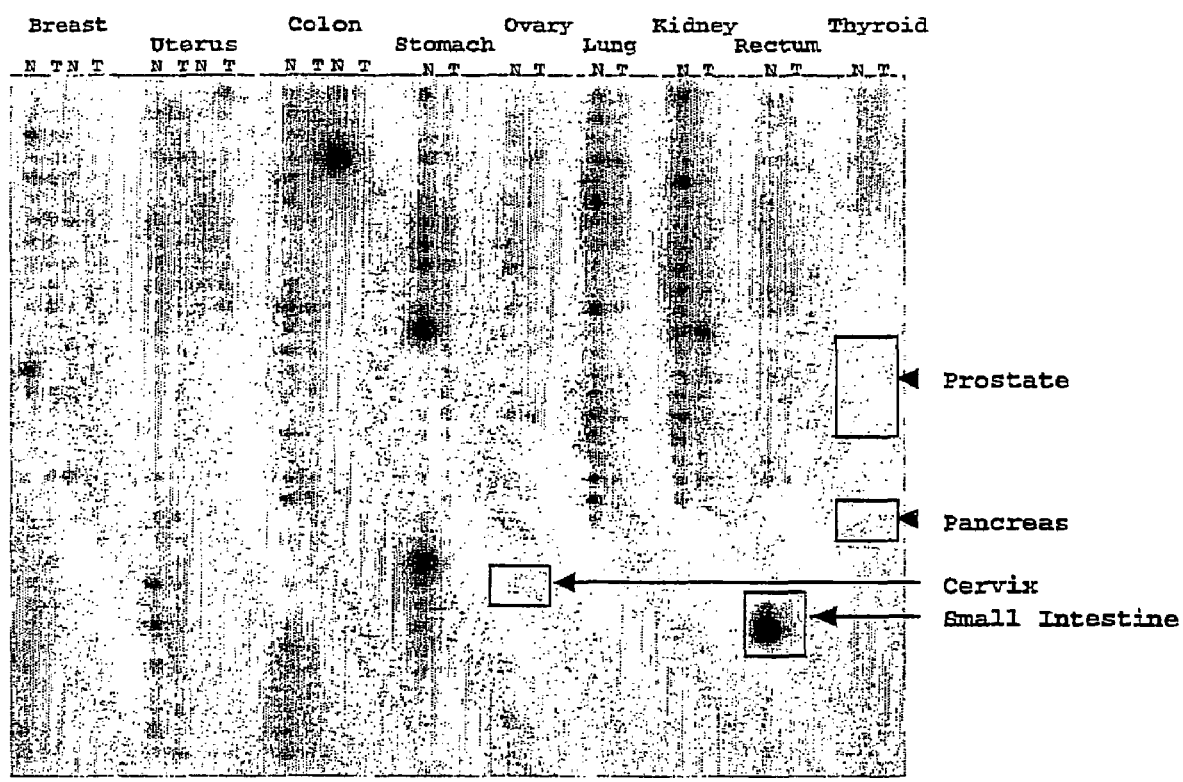
FIG. 5 shows expression of hELP transcript. Cancer Profiling Array (BD Biosciences cat. 7841-1) membranes were hybridized with 5' labeled hELP probe (nucleotides 751 to 1951). Hybridization was performed at 68° C., according to manufacturer's recommendation with a final washing using 0.2×SCC and 0.5% SDS at 68° C. for 15 min. For sample reference see BD bioscience catalog.

Summary of the data of FIG. 5.

| Cancer type | number of sample | Decrease* | Same* | Increase* |
|---|---|---|---|---|
| Breast | 50 | 36% | 46% | 18% |
| Uterus | 42 | 19% | 62% | 19% |
| Colon | 35 | 37% | 60% | 3% |
| Stomach | 27 | 52% | 37% | 11% |
| Ovary | 14 | 43% | 36% | 21% |
| Lung | 21 | 76% | 24% | 0% |
| Kidney | 20 | 60% | 35% | 5% |
| Rectum | 18 | 16% | 78% | 5% |
| Thyroid | 6 | 33% | 50% | 17% |
| Prostate | 4 | 0% | 100% | 0% |
| Pancreas | 1 | 100% | 0% | 0% |
| Cervix | 1 | 0% | 100% | 0% |
| Small Intestine | 2 | 50% | 50% | 0% |

*Tumor compared to normal tissue

Reductions in hELP mRNA expression compared with their respective normal tissues was observed in the majorities of lung, kidney and stomach cancer samples. The ELP RNA down regulation was found in around ¾ of all lung cancers and over ½ of kidney and stomach cancer samples (indication of a potential tumor supression function: "tumors want to get rid of it").

While there are shown and described presently preferred embodiments of the invention, it is to be distinctly understood that the invention is not limited thereto but may be otherwise variously embodied and practiced within the scope of the following claims.

The disclosure of all literture/publications cited throughout the specification is incorporated herein by reference in its entirety.

REFERENCES

Basler, K. and E. Hafen (1988). "Control of photoreceptor cell fate by the sevenless protein requires a functional tyrosine kinase domain." *Cell* 54(3): 299–311.

Bohni, R., J. Riesgo-Escovar, et al. (1999). "Autonomous control of cell and organ size by CHICO, a *Drosophila* homolog of vertebrate IRS1-4." *Cell* 97(7): 865–75.

Brogiolo, W., H. Stocker, et al. (2001). "An evolutionarily conserved function of the *Drosophila* insulin receptor and insulin-like peptides in growth control." *Curr Biol* 11(4): 213–21.

Caplen, N. J., J. Fleenor, et al. (2000). "dsRNA-mediated gene silencing in cultured *Drosophila* cells: a tissue culture model for the analysis of RNA interference." *Gene* 252 (1–2): 95–105.

Carbone, R., Fre, S., Iannolo, G., Belleudi, F., Mancini, P., Pelicci, P. G., Torrisi, M. R., Di Fiore, P. P. (1997). "Eps15 and eps15R are essential components of the endocytotic pathway." *Cancer Res.* 57: 5498–5504.

Chen, H., S. Fre, et al. (1998). "Epsin is an EH-domain-binding protein implicated in clathrin-mediated endocytosis." *Nature* 394(6695): 793–7.

Clemens, J. C., C. A. Worby, et al. (2000). "Use of double-stranded RNA interference in *Drosophila* cell lines to dissect signal transduction pathways." *Proc Natl Acad Sci USA* 97(12): 6499–503.

Cole (1985). *Monoclonal Antibodies and Cancer Therapy*.

Elbashir, S. M., J. Harborth, et al. (2001). "Duplexes of 21-nucleotide RNAs mediate RNA interference in cultured mammalian cells." *Nature* 411(6836): 494–498.

Elbashir, S. M., W. Lendeckel, et al. (2001). "RNA interference is mediated by 21- and 22-nucleotide RNAS." *Genes Dev* 15(2): 188–200.

Fields, S. and R. Sternglanz (1994). "The two-hybrid system: an assay for protein-protein interactions." *Trends Genet* 10(8): 286–92.

Harlow, E. and D. Lane (1988). *Antibodies, A laboratory manual*. Cold Spring Harbor, Cold Spring Harbor Laboratory.

Hidalgo, M. and E. K. Rowinsky (2000). "The rapamycin-sensitive signal transduction pathway as a target for cancer therapy." *Oncogene* 19(56): 6680–6.

Huang, H., C. J. Potter, et al. (1999). "PTEN affects cell size, cell proliferation and apoptosis during *Drosophila* eye development." *Development* 126(23): 5365–72.

Hyman, J., H. Chen, et al. (2000). "Epsin 1 undergoes nucleocytosolic shuttling and its eps15 interactor NH(2)-terminal homology (ENTH) domain, structurally similar to Armadillo and HEAT repeats, interacts with the transcription factor promyelocytic leukemia Zn(2)+ finger protein (PLZF)." *J Cell Biol* 149(3): 537–46.

Ishibashi, S., M. S. Brown, et al. (1993). "Hypercholesterolemia in low density lipoprotein receptor knockout mice and its reversal by adenovirus-mediated gene delivery." *J Clin Invest* 92(2): 883–93.

Itoh, T., S. Koshiba, et al. (2001). "Role of the ENTH domain in phosphatidylinositol-4,5-bisphosphate binding and endocytosis." *Science* 291(5506): 1047–51.

Kay, B. K., M. Yamabhai, et al. (1999). "Identification of a novel domain shared by putative components of the endocytic and cytoskeletal machinery." *Protein Sci* 8(2): 435–8.

Kay, M. A., C. N. Landen, et al. (1994). "In vivo hepatic gene therapy: complete albeit transient correction of factor IX deficiency in hemophilia B dogs." *Proc Natl Acad Sci USA* 91(6): 2353–7.

Kennerdell, J. R. and R. W. Carthew (1998). "Use of dsRNA-mediated genetic interference to demonstrate that frizzled and frizzled 2 act in the wingless pathway." *Cell* 95(7): 1017–26.

Kohler, G. and C. Milstein (1975). "Continuous cultures of fused cells secreting antibody of predefined specificity." *Nature* 256(5517): 495–7.

Kozbar (1983). *Immunology Today* 4: 72.

Landegren, U., R. Kaiser, et al. (1988). "A ligase-mediated gene detection technique." *Science* 241(4869): 1077–80.

Martin, T. F. (2001). "PI(4,5)P2 regulation of surface membrane traffic." *Current Opinion in Cell Biology* 13: 493–499.

Montgomery, M. K. and A. Fire (1998). "Double-stranded RNA as a mediator in sequence-specific genetic silencing and co-suppression." *Trends Genet* 14(7): 255–8.

Montgomery, M. K., S. Xu, et al. (1998). "RNA as a target of double-stranded RNA-mediated genetic interference in Caenorhabditis elegans." *Proc Natl Acad Sci USA* 95(26): 15502–7.

Nakashima, S., K. Morinaka, et al. (1999). "Small G protein Ral and its downstream molecules regulate endocytosis of EGF and insulin receptors." *Embo J* 18(13): 3629–42.

Nakazawa, H., D. English, et al. (1994). "UV and skin cancer: specific p53 gene mutation in normal skin as a biologically relevant exposure measurement." *Proc Natl Acad Sci USA* 91(1): 360–4.

Neufeld, T. P., A. F. de la Cruz, et al. (1998). "Coordination of growth and cell division in the *Drosophila* wing." *Cell* 93(7): 1183–93.

Newsome, T. P., B. Asling, et al. (2000). "Analysis of *Drosophila* photoreceptor axon guidance in eye-specific mosaics." *Development* 127(4): 851–60.

Ngo, H., C. Tschudi, et al. (1998). "Double-stranded RNA induces mRNA degradation in *Trypanosoma brucei*." *Proc Natl Acad Sci USA* 95(25): 14687–92.

Nurse, P. (1975). "Genetic control of cell size at cell division in yeast." *Nature* 256(5518): 547–51.

Nurse, P. (2000). "A long twentieth century of the cell cycle and beyond." *Cell* 100(1): 71–8.

Oldham, S., J. Montagne, et al. (2000). "Genetic and biochemical characterization of dTOR, the *Drosophila* homolog of the target of rapamycin." *Genes Dev* 14(21): 2689–94.

Phelps, C. B. and A. H. Brand (1998). "Ectopic gene expression in *Drosophila* using GAL4 system." *Methods* 14(4): 367–79.

Rosenthal, J. A., H. Chen, et al. (1999). "The epsins define a family of proteins that interact with components of the clathrin coat and contain a new protein module." *J Biol Chem* 274(48): 33959–65.

Sambrook, J., E. F. Fritsch, et al. (1989). *Molecular cloning: a laboratory manual*, Cold Spring Harbor Laboratory Press.

Tautz, D. and C. Pfeifle (1989). "A non-radioactive in situ hybridization method for the localization of specific RNAs in *Drosophila* embryos reveals translational control of the segmentation gene hunchback." *Chromosoma* 98(2): 81–5.

Timmons, L., D. L. Court, et al. (2001). "Ingestion of bacterially expressed dsRNAs can produce specific and potent genetic interference in *Caenorhabditis elegans*." *Gene* 263(1–2): 103–12.

Underhill, P. A., L. Jin, et al. (1996). "A pre-Columbian Y chromosome-specific transition and its implications for human evolutionary history." *Proc Natl Acad Sci USA* 93(1): 196–200.

Vaucheret, H. and M. Fagard (2001). "Transcriptional gene silencing in plants: targets, inducers and regulators." *Trends Genet* 17(1): 29–35.

Vecchi, M., S. Polo, et al. (2001). "Nucleocytoplasmic shuttling of endocytic proteins." *J Cell Biol* 153(7): 1511–7.

Verdu, J., M. A. Buratovich, et al. (1999). "Cell-autonomous regulation of cell and organ growth in *Drosophila* by Akt/PKB." *Nat Cell Biol* 1(8): 500–6.

Wagner, R. W., M. D. Matteucci, et al. (1996). "Potent and selective inhibition of gene expression by an antisense heptanucleotide." *Nat Biotechnol* 14(7): 840–4.

Weinkove, D., T. P. Neufeld, et al. (1999). "Regulation of imaginal disc cell size, cell number and organ size by *Drosophila* class I(A) phosphoinositide 3-kinase and its adaptor." *Curr Biol* 9(18): 1019–29.

Xu, T. and G. M. Rubin (1993). "Analysis of genetic mosaics in developing and adult *Drosophila* tissues." *Development* 117(4): 1223–37.

---

The invention claimed is:

1. A method for the identification of a hyperproliferative disease which comprises detecting in a body fluid or a tissue sample of a subject in need thereof a change in the expression level of an ELP protein or at least one mutation within a nucleic acid sequence encoding an ELP protein or detecting a rearrangement in the genomic elp locus wherein said change in expression level, mutation or rearrangement is indicative of hyperproliferative disease.

2. The method of claim 1 wherein said mutation is located within the DNA region coding for the ENTH domain, in the 5' untranslated region, in a codon encoding an evolutionary conserved amino acid, in the promoter or in a splicing site.

3. The method of claim 1 wherein said mutation leads to a non-functional ELP protein, to a reduced protein expression or no protein, or a fusion protein.

4. The method of claim 1, wherein said nucleic acid sequence encoding an ELP protein is selected from SEQ ID NO: 1 or a nucleic acid sequence encoding an ELP protein having the amino acid sequence as set forth in SEQ ID NO: 5.

5. The method of claim 1, wherein the disease is lung cancer.

6. The method of claim 1, wherein the disease is kidney cancer.

7. The method of claim 1, wherein the disease is stomach cancer.

* * * * *